US012664655B2

(12) United States Patent
Jailin et al.

(10) Patent No.: US 12,664,655 B2
(45) Date of Patent: Jun. 23, 2026

(54) AUTOMATIC COMPUTATION OF BPE LEVEL

(71) Applicant: GE Precision Healthcare LLC, Waukesha, WI (US)

(72) Inventors: Clement Jailin, Buc (FR); Pablo Milioni De Carvalho, Buc (FR); Laurence Vancamberg, Buc (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 280 days.

(21) Appl. No.: 18/506,911

(22) Filed: Nov. 10, 2023

(65) Prior Publication Data

US 2025/0157039 A1 May 15, 2025

(51) Int. Cl.
*G06T 7/00* (2017.01)
*A61B 6/02* (2006.01)
(Continued)

(52) U.S. Cl.
CPC ............ *G06T 7/0014* (2013.01); *A61B 6/025* (2013.01); *A61B 6/502* (2013.01); *G06T 7/62* (2017.01);
(Continued)

(58) Field of Classification Search
CPC .......... G06T 7/0014; G06T 7/62; G06T 7/68; G06T 7/0012; G06T 2207/10112;
(Continued)

(56) References Cited

U.S. PATENT DOCUMENTS 7,418,123 B2 8/2008 Giger et al.
7,848,558 B2 12/2010 Giger et al.
(Continued)

FOREIGN PATENT DOCUMENTS

CA 3142193 A1 12/2020
CN 115135230 A 9/2022
(Continued)

OTHER PUBLICATIONS

Eskreis-Winkler, S. et al., "Breast MRI Background Parenchymal Enhancement Categorization Using Deep Learning: Outperforming the Radiologist," Journal of Magnetic Resonance Imaging, vol. 56, No. 4, Oct. 2022, Available Online Feb. 15, 2022, 17 pages.
(Continued)

*Primary Examiner* — John B Strege
(74) *Attorney, Agent, or Firm* — McCoy Russell LLP

(57) ABSTRACT

Methods and systems are provided for automatically assessing a level of BPE of a patient of an imaging system based on one or more medical images of one or more breasts of the patient, using a deep learning (DL) model. The medical images may include contrast enhanced mammography (CEM) images, magnetic resonance (MR) images, or a different type of images. The one or more images may include one or more images of a same breast, where the BPE assessment outputted by the DL model may include a score, such as a percentage of BPE detected in the images. The one or more images may include images of a left breast and a right breast of the patient, where the BPE assessment outputted by the DL model may include whether an asymmetry between BPE assessments of the left breast and the right breast is detected.

16 Claims, 11 Drawing Sheets

(51) Int. Cl.

| | |
|---|---|
| *A61B 6/50* | (2024.01) |
| *G06T 7/62* | (2017.01) |
| *G06T 7/68* | (2017.01) |
| *G06V 10/764* | (2022.01) |
| *G06V 20/50* | (2022.01) |
| *G16H 30/40* | (2018.01) |

(52) U.S. Cl.

CPC .............. *G06T 7/68* (2017.01); *G06V 10/764* (2022.01); *G06V 20/50* (2022.01); *G16H 30/40* (2018.01); *G06T 2207/10112* (2013.01); *G06T 2207/20021* (2013.01); *G06T 2207/20081* (2013.01); *G06T 2207/20212* (2013.01); *G06T 2207/30068* (2013.01); *G06T 2207/30096* (2013.01); *G06V 2201/03* (2022.01)

(58) Field of Classification Search

CPC . G06T 2207/20021; G06T 2207/20081; G06T 2207/20212; G06T 2207/30068; G06T 2207/30096; G06T 2207/10116; G06T 2207/20084; G06T 2207/20221; G06T 5/50; G06T 5/92; A61B 6/025; A61B 6/502; A61B 6/481; A61B 6/5217; G06V 10/764; G06V 20/50; G06V 2201/03; G16H 30/40; G16H 50/30

See application file for complete search history.

(56) References Cited

U.S. PATENT DOCUMENTS

| | | | | |
|---|---|---|---|---|
| 9,361,683 | B2 * | 6/2016 | Highnam | .............. G06T 7/0014 |
| 9,934,588 | B2 | 4/2018 | Jo | |
| 11,302,444 | B2 | 4/2022 | Chen et al. | |
| 2020/0372637 | A1 | 11/2020 | Ha | |
| 2022/0172824 | A1 | 6/2022 | Solis | |
| 2023/0245417 | A1 * | 8/2023 | Giger | ..................... G06V 10/82 |
| | | | | 382/100 |
| 2024/0087127 | A1 * | 3/2024 | Fieselmann | .......... G06T 7/0012 |

FOREIGN PATENT DOCUMENTS

| | | | |
|---|---|---|---|
| JP | 2020183394 | A | 11/2020 |
| KR | 101659959 | B1 | 9/2016 |
| WO | 2017066827 | A1 | 4/2017 |
| WO | 2019092575 | A1 | 5/2019 |

OTHER PUBLICATIONS

"AI Provides Accurate Breast Density Classification—Technology helps discern subtle patterns in imaging," RSNA News Website, Available Online at https://www.rsna.org/news/2022/march/ai-classifies-breast-density, Mar. 17, 2022, 4 pages.

* cited by examiner

200

IMAGE PROCESSING SYSTEM 202

PROCESSOR 204

NON-TRANSITORY MEMORY 206

MODEL MODULE 208

TRAINING MODULE 210

INFERENCE MODULE 212

IMAGE DATABASE 214

DISPLAY DEVICE 234

USER INPUT DEVICE 232

900

AUTOMATIC COMPUTATION OF BPE LEVEL

TECHNICAL FIELD

Embodiments of the subject matter disclosed herein relate to systems and methods for contrast enhanced breast imaging.

BACKGROUND

Contrast enhanced imaging is a screening/diagnostic method that may be used to visualize lesions in tissue, such as breast tissue. A contrast enhancing agent is administered intravenously and may localize in lesion tissue due to rapid neovascularization around the lesion causing imperfect blood vessels which may leak the contrast agent to the surrounding tissue. The contrast enhancement is particularly useful in imaging lesions in breasts having dense breast tissue. The contrast enhancing agent may additionally be delivered to normal, healthy breast tissue and show up in a contrast enhanced image as an enhanced contrast area in a phenomena called breast background parenchymal enhancement.

BRIEF DESCRIPTION

In one embodiment, a method comprises performing an assessment of background parenchymal enhancement (BPE) of a breast of a patient based on one or more images of the breast acquired via an imaging system, using a deep learning (DL) model trained on different types of medical images of breasts; and displaying the one or more images and the BPE assessment at a display device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, herein below.

DETAILED DESCRIPTION

Figure 1:
FIG. 1 is a schematic illustration of an imaging system, in accordance with one or more embodiments of the present disclosure.
Figure 1:
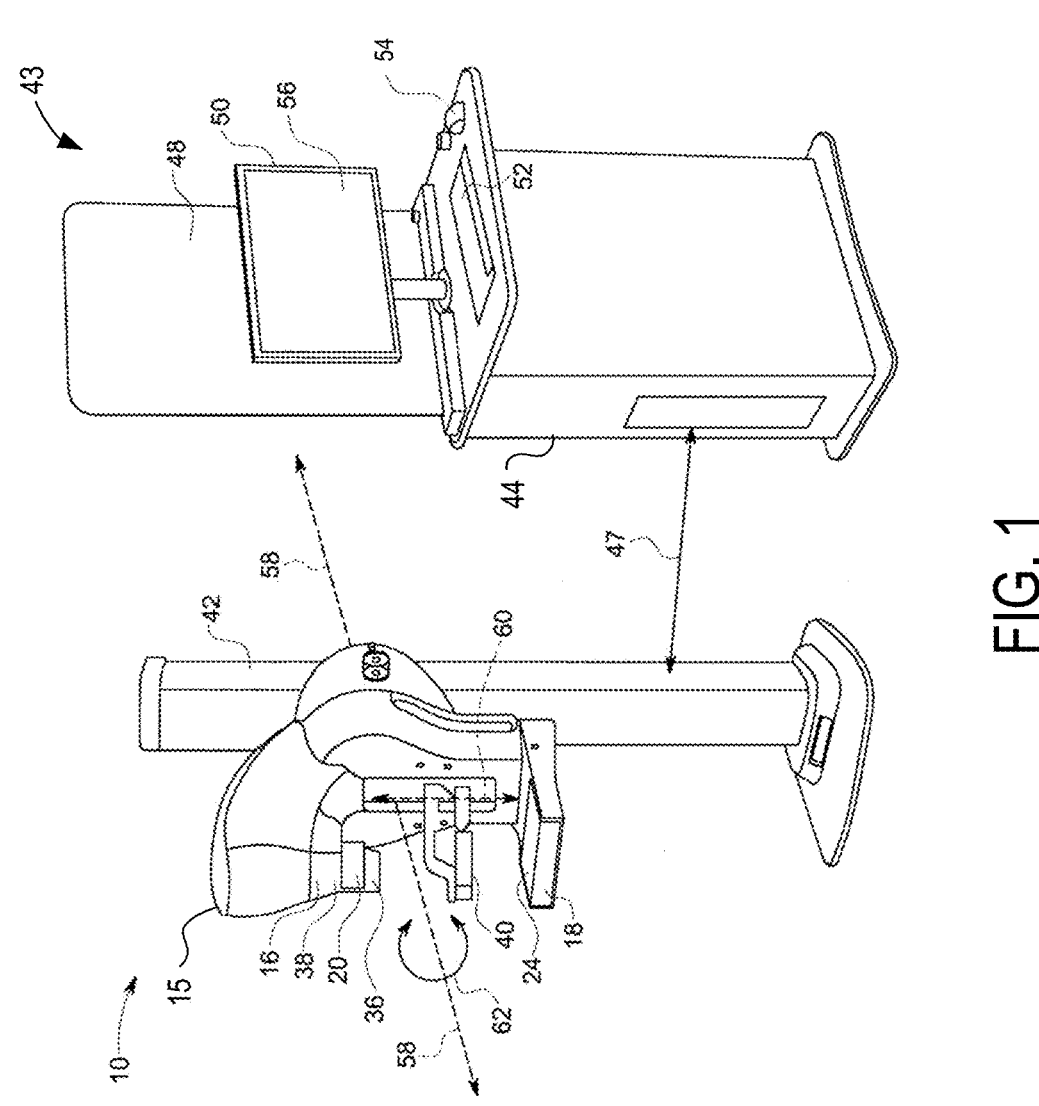

The following description relates to systems and methods for displaying contrast enhanced breast images, including two-dimensional (2D) images and three-dimensional (3D) image volumes. The contrast enhanced breast images may include images where a contrast agent is administered intravenously and preferentially localizes in lesions or other suspicious areas due to leaky neovascularized blood vessels surrounding the lesion. As a non-limiting list, the breast images may include contrast enhanced digital mammography (CEM) images, contrast enhanced digital breast tomosynthesis (CE-DBT) image volumes, CE-DBT slices (e.g., planes of the CEDBT volume), and/or CE-DBT slabs (e.g., thick slices created from a combination of CE-DBT slices), CEM biopsy images, and/or CEM synthetic 2D images (e.g., synthetic 2D images created from a CE-DBT image volume that represent in a 2D view the most important information included in the 3D image volume).

To analyze a risk of breast cancer, doctors can perform a background parenchymal enhancement (BPE) analysis. BPE may occur during CEM or contrast enhanced MRI procedures or contrast enhanced CT procedures, wherein contrast agent also localizes in normal, healthy breast tissue. A level of BPE in a breast may depend on a tissue venous blood pool and its permeability to the contrast agent. Both the level of BPE in a breast and BPE level asymmetry between breasts may be used by a clinician to aid in diagnosis and cancer risk estimation. As such, the BPE level may be indicated in a report for CEM, in accordance with clinical guidelines.

During a CEM exam, two images are acquired, a low energy (LE) and a high energy (HE) image that are recombined to produce an iodine uptake image (REC), which may show a bilateral enhancement of normal breast parenchyma after contrast administration. The breast may be categorized into four categories based on the REC image, which may be correlated to a risk of cancer and to diagnostic performances. However, the categorization of the breast BPE level is typically performed by a radiologist using a manual workflow, which may increase an amount of time taken by the radiologist in reading images and increase a use of imaging system resources. Additionally, assessing the BPE level may be difficult and may depend on an experience of the radiologist. As a result, a variability between assessments performed by different radiologists may be high. For example, a first radiologist may assess a BPE level of a medical image as moderate, while a second radiologist may assess the BPE level of the medical image as mild.

To address the high variability and to reduce the amount of time taken by the radiologist in reading images and reduce the use of imaging system resources, systems and methods are proposed herein for automatically computing and displaying a BPE assessment of one or more breasts based on one or more images using a deep learning (DL) model, such as a convolutional neural network (CNN). The automatically computed BPE assessment may be more accurate than a manual BPE assessment performed by the radiologist, resulting in a more accurate diagnosis of cancer risk and/or may aid the radiologist in detecting lesions in the breast. In contrast to the ML models used for breast density assessment, the proposed DL model may take a plurality of images of the breast as input. For example, the DL model may take both the low energy image (LE) and the recombined image (REC) of the CEM exam as input, and output a BPE assessment based on both of the LE image and the REC image. The LE image and the REC image may be generated during a same breast examination, by adjusting an X-ray beam of the imaging system between acquisitions. An additional advantage of the proposed approach is that an efficiency of an overall process for reading mammograms may be increased, resulting in faster diagnoses and improved patient care. Further, the output of the DL model may be used to analyze whether an asymmetry in BPE between a right breast and a left breast of a patient is present, and/or to analyze whether there is an inconsistency in BPE across different images of a same breast.

Figure 2:
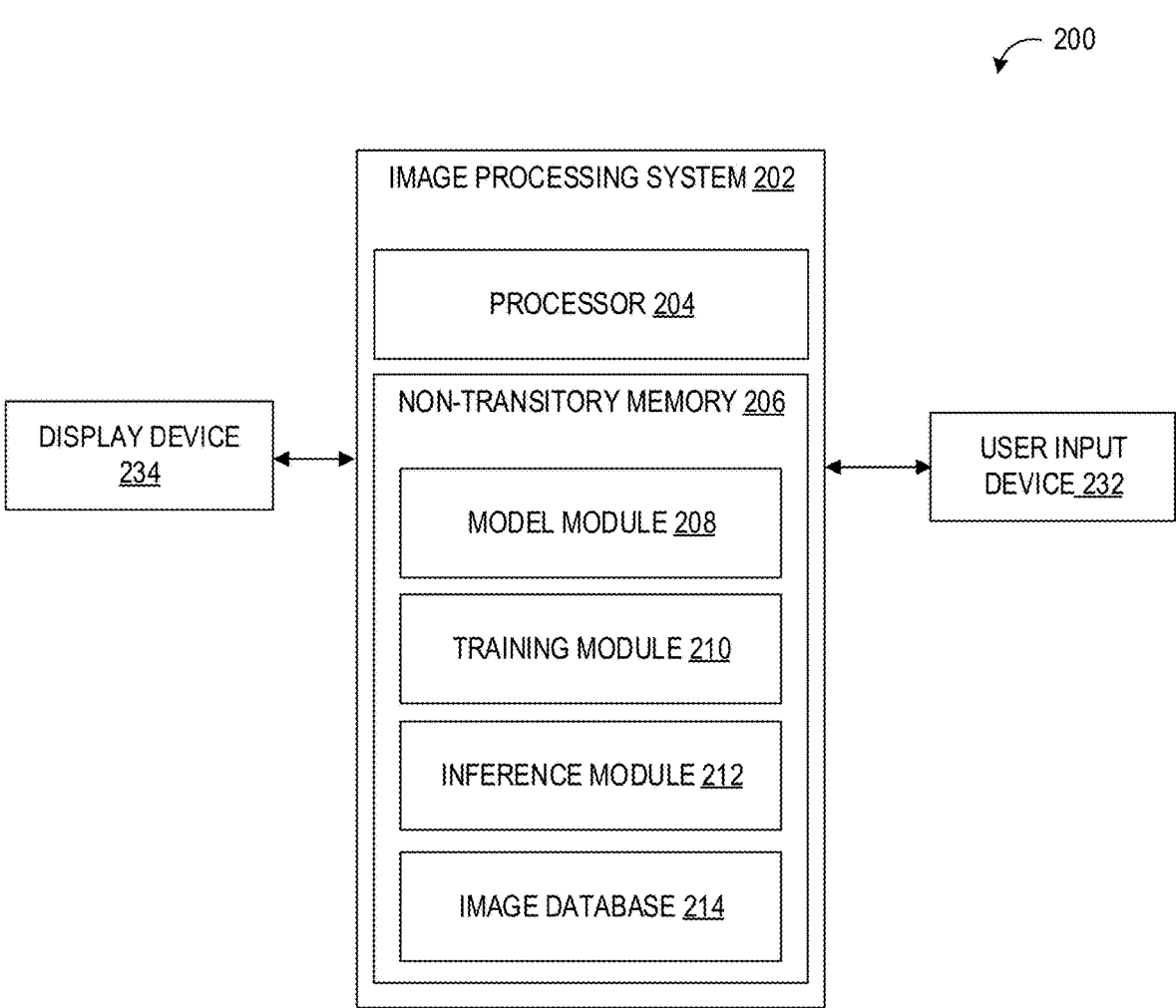
FIG. 2 is an image processing system, in accordance with one or more embodiments of the present disclosure.
Figure 9:
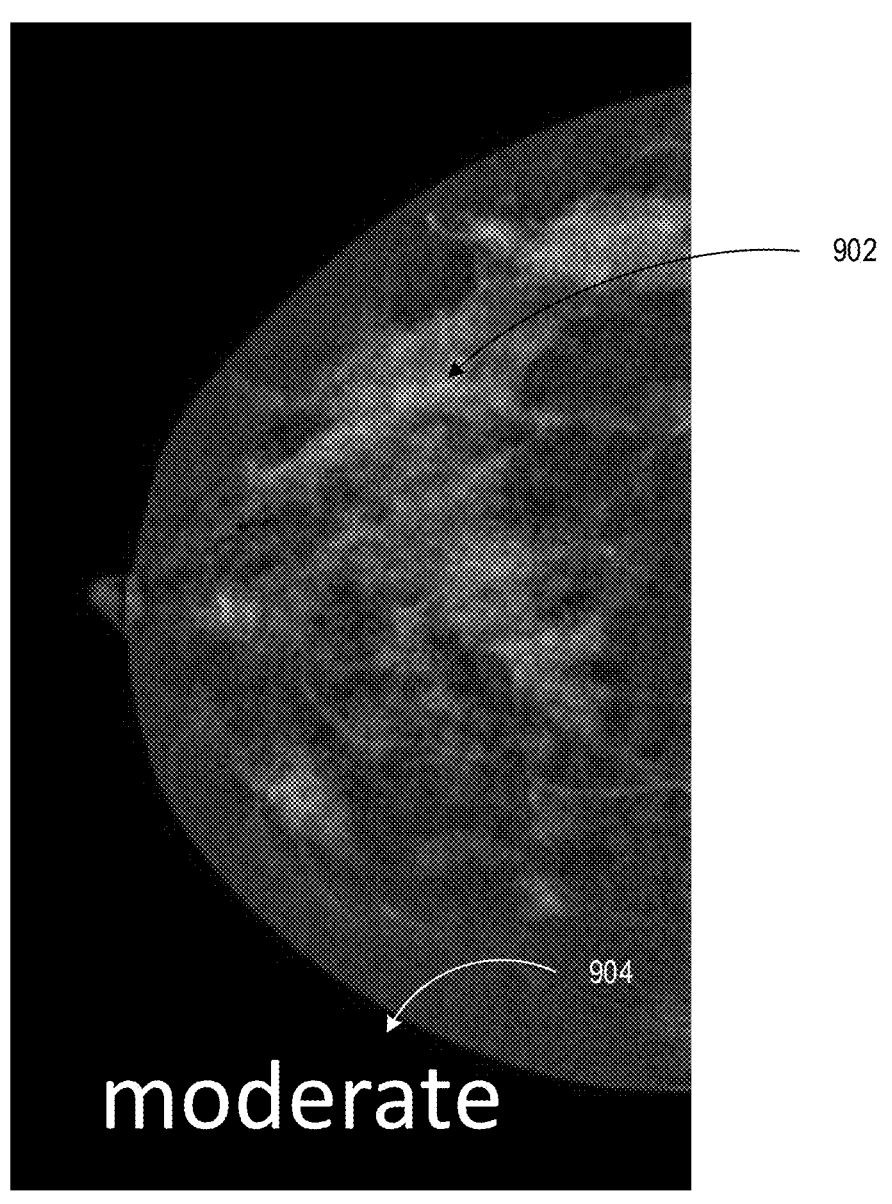
FIG. 9 is a first exemplary image of a breast including a first type of BPE assessment, in accordance with one or more embodiments of the present disclosure.
Figure 10:
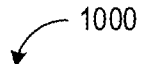
FIG. 10 is a second exemplary image of the breast including a second type of BPE assessment, in accordance with one or more embodiments of the present disclosure.
Figure 10:
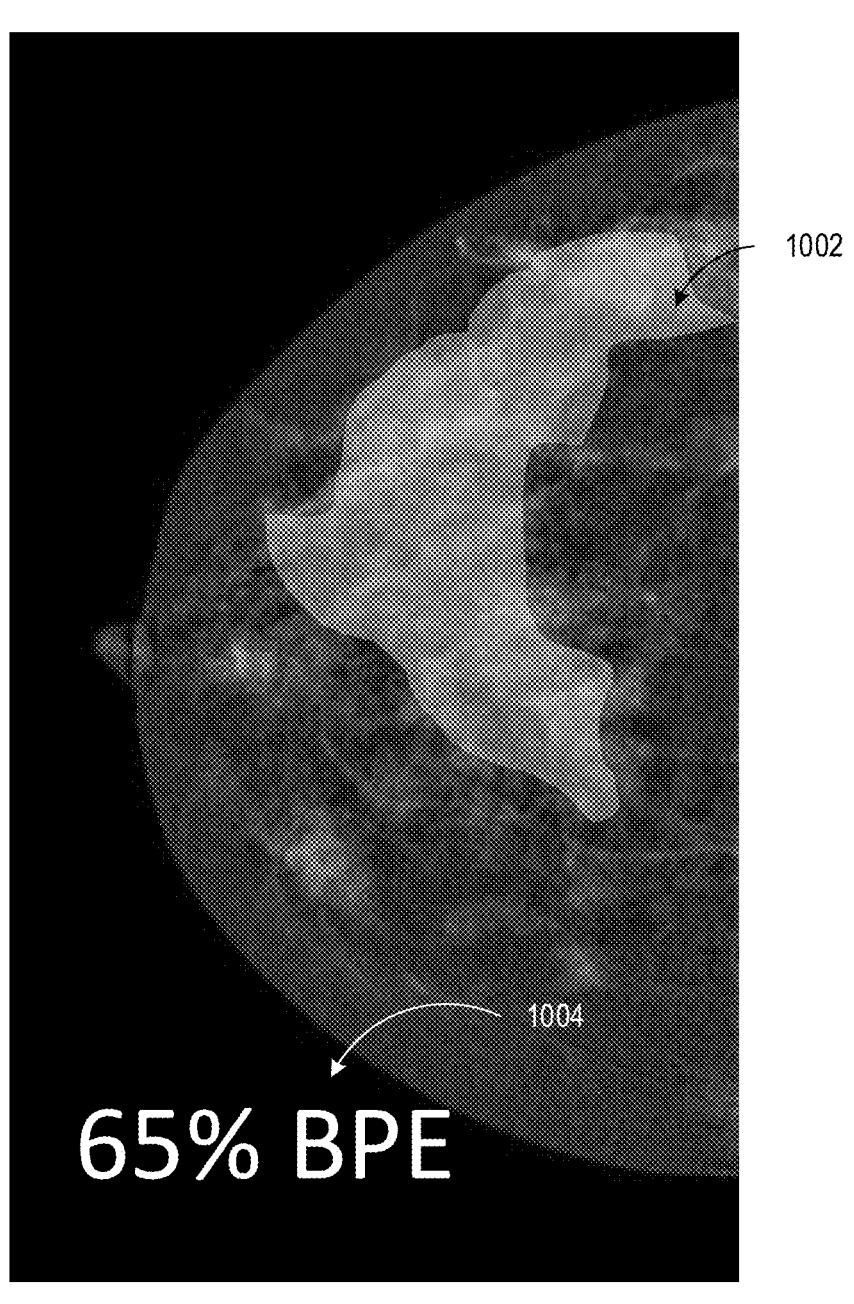
Figure 11:
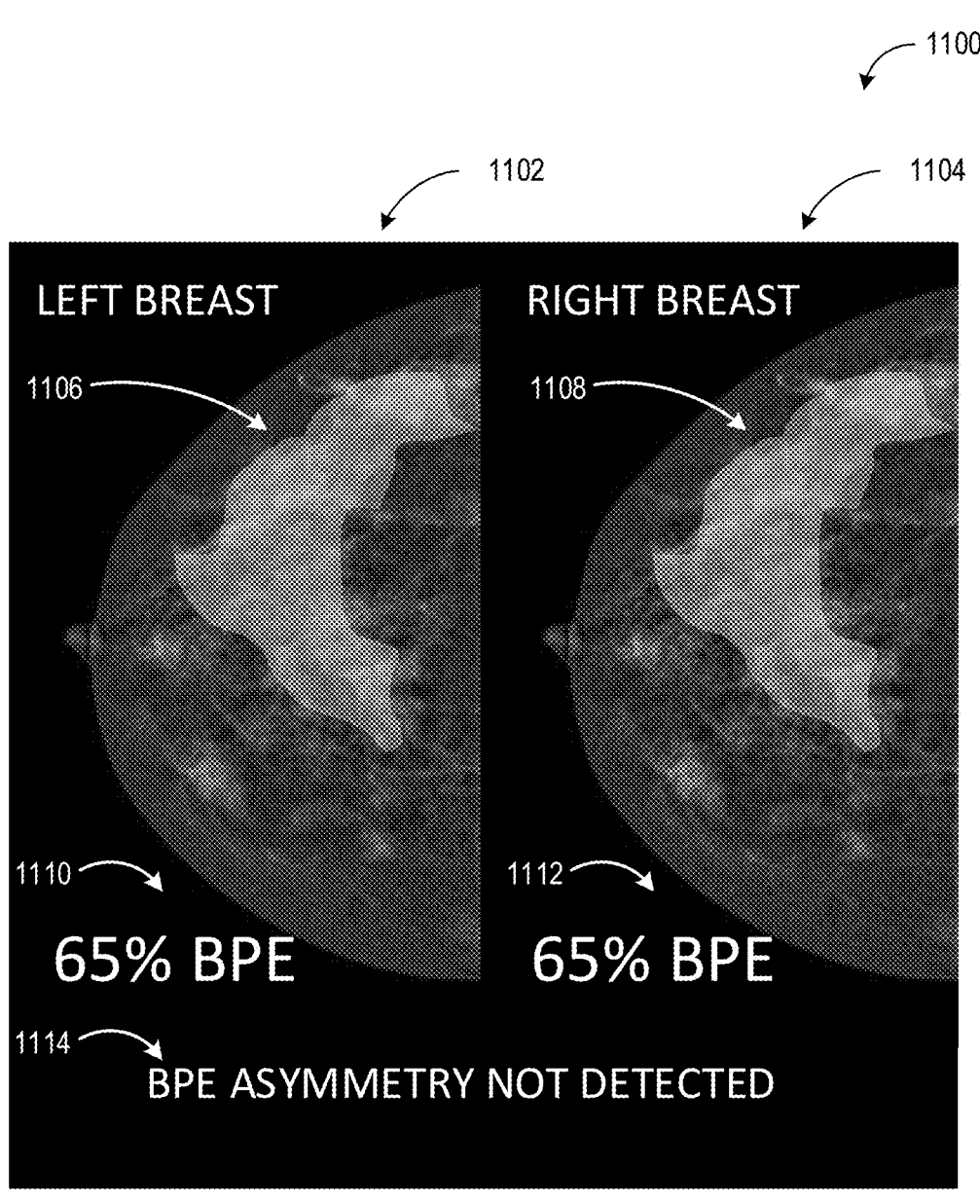
FIG. 11 shows an exemplary display of two breasts of a patient where a BPE asymmetry was not detected, in accordance with one or more embodiments of the present disclosure.

A block diagram of an image processing system which may store one or more methods for identifying and displaying LE. HE, and/or REC images (all referred to herein as CEM images) is shown in FIG. 2. The image processing system may be communicatively coupled to an imaging system which may be a digital mammography system, or a DBT imaging system. A schematic of the imaging system is shown in FIG. 1. The imaging system may be used to generate contrast uptake images which may be displayed on a display device of the imaging system. The displayed image may be automatically processed by the image processing system, and the image may be updated as a result of the processing. In particular, the image processing system may automatically compute a BPE level of the breast in the image using a DL model, and display the computed BPE level in the image on the display device. The DL model may be trained in accordance with the method of FIG. 5, within a training system such as the training system depicted in FIG. 3. After training, the DL model may be applied to a contrast uptake breast image, such as those obtained during a CEM exam, by following one or more steps of the method of FIG. 6. An example of a contrast uptake image including BPE is shown in FIG. 4. Further, BPE assessments made by the DL model for a left breast of a patient and a right breast of the patient may be compared, using the methods of FIGS. 7 and 8. Example displays of contrast uptake images including outputs of the DL model are shown in FIGS. 9, 10, and 11.

Turning now to FIG. 1, an imaging system 100 including an x-ray system 10 for acquiring an image of a breast is shown, according to one or more embodiments of the disclosure. In some examples, the x-ray system 10 may be a digital mammography system, or a tomosynthesis system, such as a digital breast tomosynthesis (DBT) system. Further, the x-ray system 10 may be used to perform one or more procedures including digital tomosynthesis imaging, DBT guided breast biopsy and CEM exams.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree in either direction about the axis 58. For example, the angular range of rotation of the radiation source 16 may be $-\theta$ to $+\theta$, where $\theta$ may be such that the angular range is a limited angle range, less than 360 degrees. An exemplary x-ray system may have an angular range of $\pm 11$ degrees, which may allow rotation of the gantry (that is rotation of the radiation source) from $-11$ degrees to $+11$ degrees about an axis of rotation of the gantry. The angular range may vary depending on the manufacturing specifications. For example, the angular range for DBT systems may be approximately $\pm 11$ degrees to $\pm 60$ degrees, depending on the manufacturing specifications.

The radiation source 16 is directed toward a volume or object to be imaged and is configured to emit radiation rays at desired times to acquire one or more images. The radiation detector 18 is configured to receive the radiation rays via a surface 24. The radiation detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some embodiments, the x-ray system 10 may further include a patient shield 36 mounted to the radiation source 16 via face shield rails 38 such that a patient's body part (e.g., head) is not directly under the radiation. The x-ray system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the radiation detector 18, and a distance between the radiation detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part and hold the body part still in place while optionally providing apertures to allow for insertion of a biopsy needle, such as a core needle or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The imaging system 100 may further include workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In an embodiment, the communication between the controller and the x-ray system 10 may be via a wireless communication system. In other embodiments, the controller 44 may be in electrical communication with the one or more components of the x-ray system via a cable 47. Further, in an exemplary embodiment, as shown in FIG. 1, the controller 44 is integrated into workstation 43. In other embodiments, the controller 44 may be integrated into one or more of the various components of the system 10 disclosed above. Further, the controller 44 may include processing circuitry that executes stored program logic and may be any one of different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

Controller 44 may adjust the operation and function of the x-ray system 10. As an example, the controller 44 may provide timing control, as to when the x-ray source 16 emits x-rays, and may further adjust how the radiation detector 18 reads and conveys information or signals after the x-rays hit the radiation detector 18, and how the x-ray source 16 and the radiation detector 18 move relative to one another and relative to the body part being imaged. The controller 44 may also control how information, including images and data acquired during the operation, is processed, displayed, stored, and manipulated. Various processing steps as described herein with respect to FIGS. 2 and 3, performed by the controller 44, may be provided by a set of instructions stored in non-transitory memory of controller 44.

Further, as stated above, the radiation detector 18 receives the radiation rays emitted by the radiation source 16. In particular, during imaging with the x-ray system, a projection image of the imaged body part may be obtained at the radiation detector 18. In some embodiments, data, such as projection image data, received by the radiation detector 18 may be electrically and/or wirelessly communicated to the controller 44 from the radiation detector 18. The controller 44 may then reconstruct or recombine one or more scan images based on the projection image data, by implementing a reconstruction algorithm or a recombination algorithm, for example. The reconstructed or recombined image may be displayed to the user on the user interface 56 via the display 50 (e.g., a screen).

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the radiation detector 18 and the compression paddle 40. Thus, a volume of the x-ray system 10 between the compression paddle 40 and the radiation detector 18 is an imaging volume. The radiation source 16 then emits radiation rays onto the compressed breast, and a projection image of the breast is formed on the radiation detector 18. The projection images may then be reconstructed or recombined by the controller 44, and displayed on the display 50. During mammography, the gantry 15 may be adjusted at different angles to obtain images at different orientations, such as a cranio-caudal (CC) image and a medio-lateral oblique (MLO) image. In one example, the gantry 15 may be rotated about the axis 58 while the compression paddle 40 and the radiation detector 18 remain stationary. In other examples, the gantry 15, the compression paddle 40, and the radiation detector 18 may be rotated as a single unit about the axis 58.

In some examples, breast imaging systems such as imaging system 100 may be configured to perform contrast enhanced imaging where contrast agents, such as iodine, can be injected into the patient that travel to the region of interest (ROI) within the breast (e.g., a lesion). The contrast agents are taken up in the blood vessels surrounding a cancerous lesion in the ROI, enhancing the ability to locate the lesion. In some examples, the contrast agent may additionally be taken up by healthy breast tissue causing BPE to be visible in the acquired image.

The use of a contrast agent can be coupled with images of the ROI taken using dual-energy imaging processes and technology. In dual-energy imaging, low-energy (LE) and high-energy (HE) images are taken of the breast containing the ROI. For each view, a pair of images is acquired: a low-energy (LE) image and a high-energy (HE) image. The LE and HE images are usually obtained at mean energies above and below the k-edge of the contrast agent. At x-ray energies just above the k-edge of the contrast agent, the absorption of x-rays of the contrast agent is increased, resulting in a difference in signal intensity between LE and HE image. The LE and the HE images are therefore recombined to produce a REC image corresponding to an iodine uptake image.

In dual-energy 3D or stereotactic procedures, LE and HE image acquisitions are performed, with at least two different positions of the x-ray source with respect to the detector. The images are then recombined to display iodine uptake information with regard to the internal structure of the tissue being imaged. The contrast agent may pool in healthy breast tissue causing BPE.

An example of a REC image 400 of a breast is shown in FIG. 4. The breast in REC image 400 does not include a lesion or other type of suspicious area. However, REC image 400 includes a region 402 which is shown as increased contrast (e.g. lighter) than surrounding breast tissue. Region 402 may be due to BPE. BPE may be healthy tissue, but levels of BPE may be linked to risk for developing cancerous lesion. For this reason, a clinician may also be interested in identifying BPE in a REC image or other contrast enhanced image in addition to or instead of identifying a suspicious area.

FIG. 2 shows a block diagram 200 of an image processing system 202, in accordance with an embodiment. In some embodiments, image processing system 202 is incorporated into the imaging system 100. In some embodiments, at least a portion of image processing system 202 is disposed at a device (e.g., edge device, server, etc.) communicably coupled to the imaging system 100 via wired and/or wireless connections. In some embodiments, at least a portion of image processing system 202 is disposed at a separate device (e.g., a workstation) which can receive images from the imaging system 100 or from a storage device which stores the images/data generated by the imaging system 100. Image processing system 202 may be operably/communicatively coupled to a user input device 232 and a display device 234. User input device 232 may comprise the user interface 56 of the imaging system 100, while display device 234 may comprise the display device 50 of the imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a model module 208, a training module 210, an inference module 212, and an image database 214. Model module 208 may include at least one machine learning (ML) and/or deep learning (DL) model, and instructions for implementing the at least one DL model to automatically assess a level of BPE of a breast based on an image of the breast, as described in greater detail below. Model module 208 may include models of various types, including trained and/or untrained neural networks such as CNNs, statistical models, or other models, and may further include various data, or metadata pertaining to the one or more models stored therein.

Non-transitory memory 206 may further store a training module 210, which may comprise instructions for training the at least one DL model stored in model module 208. In particular, training module 210 may include instructions that, when executed by processor 204, cause image processing system 202 to conduct one or more of the steps of method 500 for training a neural network model, discussed in more detail below in reference to FIG. 5. In some embodiments, training module 210 may include instructions for implementing one or more gradient descent algorithms, applying one or more loss functions, and/or training routines, for use in adjusting parameters of one or more neural networks of model module 208. Training module 210 may include training datasets for the one or more models of model module 208.

Non-transitory memory 206 also stores an inference module 212. Inference module 212 may include instructions for deploying a trained DL model, for example, to automatically assess a level of BPE of a breast based on an image of the breast. In particular, inference module 212 may include instructions that, when executed by processor 204, cause image processing system 202 to conduct one or more of the steps of method 600 of FIG. 6, as described in further detail below.

Non-transitory memory 206 further stores image database 214. Image database 214 may include for example, images acquired via the imaging system 100. Image database 214 may include various types of medical images used in one or more training sets for training the one or more neural networks of model module 208.

In some embodiments, non-transitory memory 206 may include components disposed at two or more devices, which may be remotely located and/or configured for coordinated processing. In some embodiments, one or more aspects of non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an image to use in training a DL model, or for further processing using a trained DL model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an imaging system 100, and/or interact with various data stored in non-transitory memory 206.

It should be understood that image processing system 202 shown in FIG. 2 is for illustration, not for limitation. Another appropriate image processing system may include more, fewer, or different components.

Figure 3:
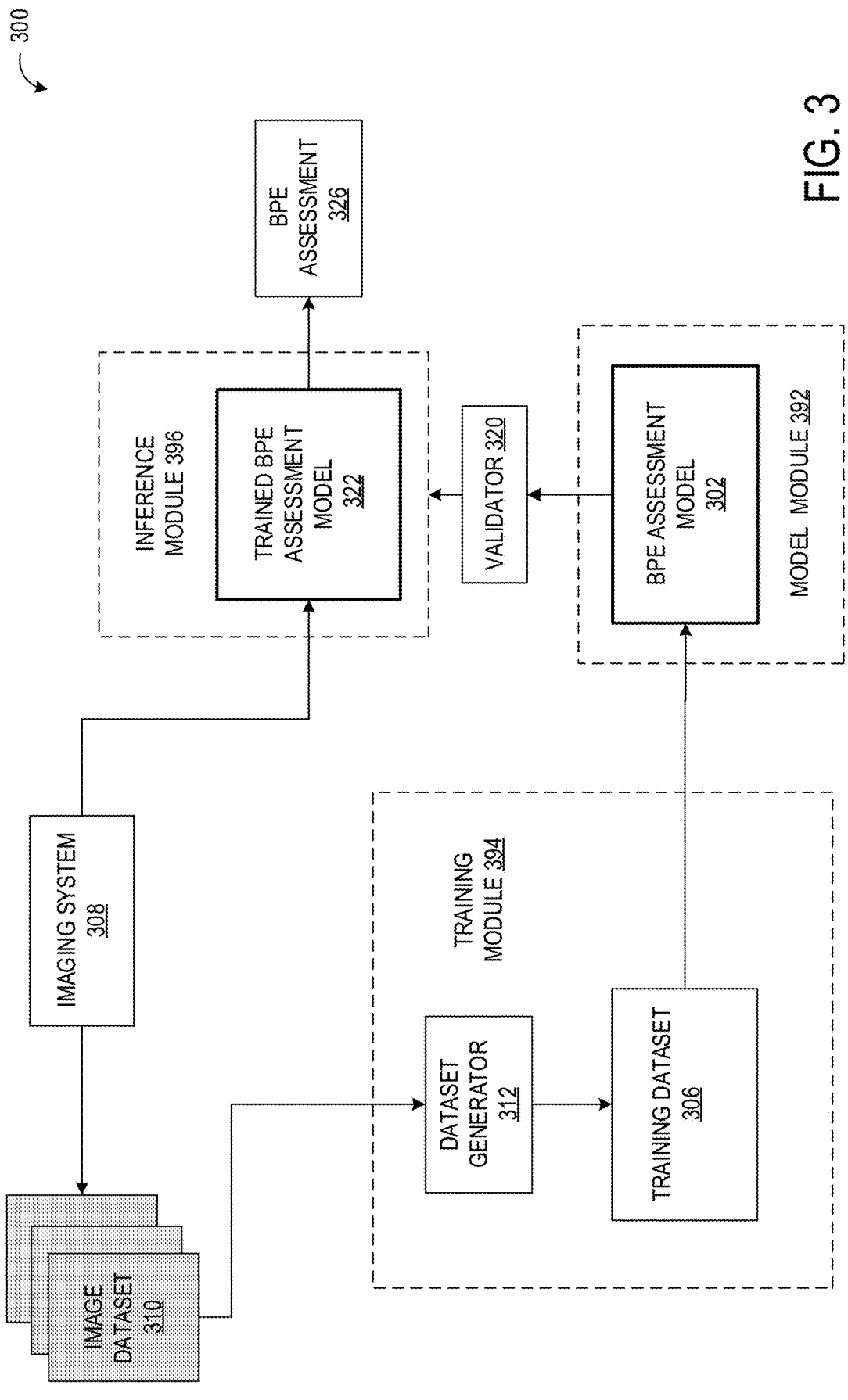
FIG. 3 is a block diagram showing a training system for a deep learning (DL) model, in accordance with one or more embodiments of the present disclosure.
Figure 4:
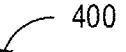
FIG. 4 is a medical image showing background parenchymal enhancement (BPE), as prior art.
Figure 4:
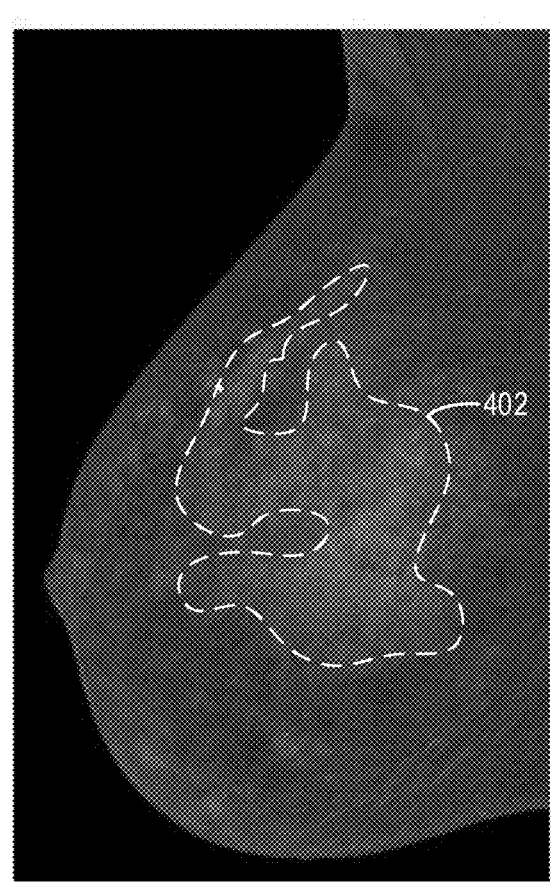

Referring to FIG. 3, an example of a BPE assessment model training system 300 is shown. BPE assessment model training system 300 may be implemented by an image processing system, such as image processing system 202 of FIG. 2, to train a DL model to automatically assess a level of BPE of a breast based on one or more images of the breast. In an embodiment, BPE assessment model training system 300 includes an BPE assessment model 302, to be trained, which may be part of a model module 392 of the image processing system (e.g., model module 208 of FIG. 2).

BPE assessment model 302 may be trained on a training dataset 306, which may be stored in a training module 394 (e.g., training module 210 of FIG. 2). Training dataset 306 may comprise a plurality of training pairs. Each training pair may comprise at least one input image including a breast, and at least one corresponding image of the breast with the BPE segmented and/or a corresponding BPE level of the breast as ground truth. The input images may be obtained from an image dataset 310, which may include CEM images, CE-DBT image volumes/slices/slabs, CEM biopsy images, and/or 2D synthetic images of a breast generated from various breast examinations performed on various subjects using an imaging system, such as imaging system 308 and/or imaging system 100 of FIG. 1. In some examples, image dataset 310 may be stored in image database of the image processing system (e.g., image database 214). Alternatively, in some embodiments, image dataset 310 may be an external image dataset, such as a public dataset of mammograms.

The input images may include LE images, REC images, and/or both REC images and LE images, and/or other types of medical images described above. In one embodiment, a REC image (e.g., contrast uptake image) and an LE image (e.g., a morphological image) may be included as inputs in a training pair, where both of the REC image and the LE image would be inputted simultaneously into BPE assessment model 302. The REC image and the LE image may be generated during a single breast examination, for example, by adjusting an X-ray (e.g., X-ray system 10 of FIG. 1) of the imaging system between acquiring the high energy image and the low energy image. In another embodiment, one or more CE-DBT images, or CEM biopsy images may be included as inputs in a training pair. During a CEM or CE-DBT exam, the breast can be imaged at various rotation angles of the mammography system. For example, during a CEM exam, two views may be acquired: a craniocaudal view (CC), and a mediolateral oblique (MLO) view. A BPE assessment may be generated per patient, where BPE assessment model 302 may use as input various images of the exam for both breasts of the patient and different views (CC/MLO). A BPE assessment may also be generated for a breast, where BPE assessment model 302 may use as input various images of one breast acquired in the different views (CC/MLO). During a CEM or CE-DBT exam, and to compute a global BPE level or score per breast and patient, injection timing (a time of when contrast is injected) and acquisition timing information (times that images of breasts are acquired) may be used. As one example, a BPE score for a breast may be a maximum of a first BPE score of the breast based on a CC image and a second BPE score of the breast based on an MLO image. As another example, the BPE score for the breast may be calculated as a function of the first BPE score of the breast based on the CC image, the second BPE score of the breast based on the MLO image, a first time at which the CC image is generated, a second time at which the MLO image is generated, and/or a time at which the contrast was injected.

Training module 394 may include a dataset generator 312, which may generate the training pairs of training dataset 306. Generating the training pairs may include labeling input images of image dataset 310 with a ground truth BPE assessment. In various embodiments, the ground truth BPE assessment may include a BPE score, where the score is an estimated percentage of tissues of a breast showing BPE, with respect to a surface (e.g., in the case of 2D imaging) or volume (e.g., in the case of 3D imaging, such as CE-DBT) of the breast. When estimated with respect to the volume of the breast, the estimated percentage of tissues of the breast showing BPE may be expressed with respect to a total glandular tissue volume, or a whole breast volume. The surface or volume of the breast may be estimated via a breast surface/volume extractor. For example, if 65% of the breast tissues of the breast show BPE, the BPE score may be 65%. In other embodiments, the ground truth BPE assessment may include a BPE classification rather than a score. For example, the BPE classification may include four categories in accordance with the Breast Imaging Reporting and Data System (BIRADS) lexicon: minimal, mild, moderate, and marked, based on intensity and a pattern observed. In some embodiments, a + or a − may be added to generate eight categories based on the BIRADS lexicon (e.g., minimal +/−, mild+/−, moderated +/−, marked +/−).

In some examples, the input images may be assigned the ground truth BPE scores during a manual procedure, where human experts (e.g., radiologists) estimate the BPE levels of the input images. In some embodiments, ground truth images with BPE segmented may be included in the training pairs, and BPE assessment model 302 may learn to segment the BPE in the input images. The ground truth BPE segmented images may be generated by a segmentation model, or manually generated.

In some embodiments, the training pairs may include additional input data. For example, in a first embodiment, a training pair may include a single input image, a version of the single input image with BPE segmented, as ground truth data, and a corresponding ground truth label (BPE score). In a second embodiment, a training pair may include two input images of the same breast (e.g., a REC image and a LE image), ground truth versions of the two input images with BPE segmented, and a ground truth BPE score for both of the two input images. The LE image may be used to determine whether an enhancement is BPE or an artefact. In a third embodiment, a training pair may include one or more input images and encodings of other relevant clinical data of a patient of the breast and ground truth data. For example, some studies have suggested that BPE may represent physiological hormonal enhancement, reflecting hormone-related changes in breast composition and vascularity. As one example, fluctuations in BPE have been demonstrated throughout the menstrual cycle (with the highest levels of enhancement in the second half of the menstrual cycle during the luteal phase when breast cell proliferation is at its highest). BPE has also been demonstrated to reflect variations in oestrogen-mediated vascular permeability, with increased BPE seen in women taking oestrogen replacement therapy, and decreased BPE with anti-oestrogen medications and in postmenopausal patients. Thus, the training pair may include an encoding of where the patient is with respect to a menstrual cycle, a menopausal status, or encodings of treatment related information, such as comparisons between pre-neoadjuvant therapy treatment images and post-neoadjuvant treatment images. The encodings may be inputted into the train BPE assessment model 302 along with the input image(s).

Further, in some embodiments, the training pairs may include a first image (or set of recombined and low energy images, CE-DBT image volumes, etc.) of a first (e.g., left) breast of a patient, and a second image (or set of recombined and low energy images, CE-DBT image volumes, etc.) of a second (e.g., right) breast of the patient, and BPE assessment model 302 may be trained to output an assessment of whether an asymmetry exists between a first BPE of the first breast and a second BPE of the second breast. The asymmetry may exist if a difference between the first BPE and the second BPE is greater than a threshold difference, such as, for example, 5%. For example, if the first BPE is 65%, and the second BPE is 55%, the difference between the first BPE and the second BPE is 10%, which is greater than the threshold of 5%, whereby the BPE asymmetry between the first breast and the second breast exists. In other embodiments, BPE asymmetry may be determined by a separate asymmetry detection module based on BPE assessments of left and right breasts, as described in greater detail below in FIG. 7.

During a CEM or CE-DBT exam, contrast agent circulates inside the breast, so the level of BPE is function of time and patient physiology. Multiple views of the breasts may be acquired at different timings. As a result, a level of iodine inside the breast may vary for the different acquisitions. Thus, to a certain extent, it is expected that the level of BPE may vary between breasts (left/right images) and between different views (e.g., CC/MLO) acquired during the exam. Optionally, a late additional view such as a mediolateral view ML may be acquired, where a delay is imposed (e.g., more than 5 minutes) before acquiring the image after the injection and the initial views. In this case, because of a wash-out of the contrast agent, it may also be expected that the BPE level could be different from the other views acquired between 2 and 7 minutes after injection. To take into account this natural phenomena, the asymmetry detection module may take into account the injection time and the image acquisition time to produce the asymmetry results.

Once the training pairs of training dataset 306 have been generated, the training pairs may be assigned to either a training dataset, validation dataset, or a test dataset. Each training pair may include a plurality of input images, a respective plurality of ground truth BPE segmented versions of the input images, and/or a respective plurality of ground truth BPE assessments/scores. The training dataset may be used for the optimization of the BPE assessment model 302. The validation dataset may be used to prevent overfitting, whereby BPE assessment model 302 learns to map features specific to samples of the training set that are not present in the validation set. The test dataset may be used to estimate the model's performance in deployment. The number of training pairs in the test and validation datasets may be less than the number of training pairs in the training dataset.

BPE assessment model training system 300 may be implemented to train BPE assessment model 302 to learn to predict a BPE level of breasts included in the input images. BPE assessment model 302 may be configured to receive the training pairs from the training module 394 and output the predicted BPE level. One or more parameters of BPE assessment model 302 may then be iteratively adjusted to minimize a loss function, based on a difference between the outputted predicted BPE level and the target BPE level included in the relevant training pair, until an error rate decreases below a first threshold error rate. Training of BPE assessment model 302 is described in greater detail below, in reference to FIG. 5.

In various embodiments, the input images may be inputted into BPE assessment model 302 as a 2D or 3D array of image values (e.g., pixels with an x/y position or voxels with an x/y/z position). In other words, each data value of each pixel/voxel of each input image may be inputted into an input node of BPE assessment model 302. The image values may correspond to two images, one for an LE image and one for a REC image. That is, a first 2D array of image values representing the LE image may be a first set of inputs into BPE assessment model 302, and a second 2D array of image values representing the REC image may be a second set of inputs into BPE assessment model 302. Alternatively, the image values may correspond to one or more CE-DBT image volumes, where a 3D array of image values representing a CE-DBT image volume may be a set of inputs into BPE assessment model 302.

BPE assessment model training system 300 may include a validator 320 that validates a performance of BPE assessment model 302. Validator 320 may take as input a trained or partially trained BPE assessment model 302 and a validation dataset of training pairs. If the error rate of the trained or partially trained BPE assessment model 302 on the validation dataset of training pairs decreases below a second threshold error rate, the performance of the trained or partially trained BPE assessment model 302 may be validated, whereby a training stage of the trained or partially trained BPE assessment model 302 may end.

BPE assessment model training system 300 may include an inference module 396, which comprises a trained BPE assessment model 322 that has been validated by validator 320 as described above. Inference module 396 may also include instructions for deploying trained BPE assessment model 322 to perform a BPE assessment (e.g., predict a BPE level) of a breast in a new (e.g., not included in image dataset 310) 2D or 3D medical image (e.g., contrast enhanced mammogram). The new medical image may be generated by imaging system 308 during a patient breast exam, for example. Specifically, trained BPE assessment model 322 may receive the new 2D medical image as input, and may output a BPE assessment 326. In various embodiments, BPE assessment 326 may be displayed on a display device of the imaging system 308. For example, BPE assessment 326 may be displayed superimposed on the new medical image, as shown in FIGS. 9-11.

Figure 5:
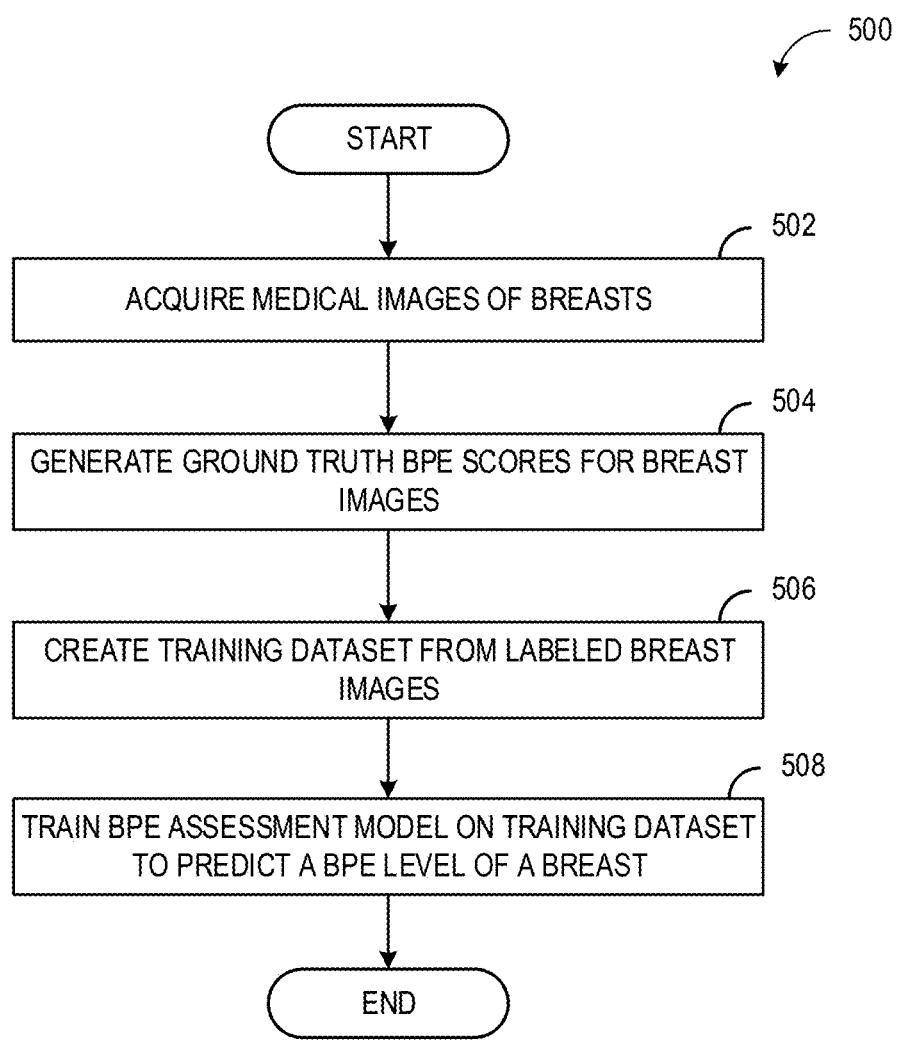
FIG. 5 is a flowchart illustrating a method for training the DL model to perform a BPE assessment of an image, in accordance with one or more embodiments of the present disclosure.

Referring now to FIG. 5, an exemplary method 500 is shown for training a BPE assessment model (e.g., BPE assessment model 302 of FIG. 3) to assess a BPE level of a breast based on an image of the breast. Method 500 may be carried out by a training module and/or a model module of an BPE assessment model training system, such as training module 394 and model module 392 of BPE assessment model training system 300. The BPE assessment model training system may be included in an image processing system, such as image processing system 202, and one or more instructions of method 500 may be executed by a processor of the image processing system (e.g., processor 204). In various embodiments, the image processing system may be coupled to an imaging system such as imaging system 100 of FIG. 1.

Method 500 begins at 502, where method 500 includes acquiring a plurality of medical images of breasts. In some embodiments, the medical images may include 3D image volumes, such as CE-DBT image volumes via a DBT system. In other embodiments, the medical images may include 2D images, such as CEM images via a digital mammography system, or slices/slabs or CEM synthetic 2D images generated from a CE-DBT image volume. The medical images may also include CEM biopsy images. In various embodiments, the images may include breast morphological (LE) images and/or contrast uptake images from the imaging system, or from an image dataset (e.g., image dataset 310) generated using the imaging system, or via a different source. The morphological images may be images in which a contrast agent is not captured in the image, and the contrast uptake images may include images in which the contrast agent is captured in the image. The morphological images may be LE images, and the contrast uptake images may include REC images resulting from a recombination of LE images and high energy x-ray images. The contrast uptake images may include REC images acquired during a contrast enhanced mammography exam. Acquiring a CEM exam may include, before acquiring the images, intravenous administration of a contrast agent followed by image capture. A processing device, such as a controller of the imaging system, may include instructions to generate a recombined image from the low energy image and the high energy image. The recombination instructions may include performing a logarithmic weighted subtraction between the low energy image and the high energy image. The contrast uptake image may include regions of interest where contrast media has accumulated which may be observed as areas of increased contrast compared to a background contrast of the recombined image. The morphological images and contrast uptake images may be 2D or 3D images.

At 504, method 500 includes generating ground truth BPE assessments for each of the acquired breast images. In various embodiments, assigning the ground truth BPE assessments may be performed by human experts. The human experts may provide labels, such as, for example, minimal/mild/moderate/marked, or a score, as described above. Additionally, the human experts may provide a version of one or more input images where regions of BPE are segmented. In some embodiments, the annotations provided by the human experts may be combined to create a ground truth (e.g. overlapping intersection, a mean or function of different scores, a most commonly appearing label, etc.) or the DL may take a plurality ground truth data. At 506, method 500 includes creating a training dataset (e.g., training dataset 306) including a plurality of training pairs, where each training pair includes at least one or more input images and a corresponding ground truth BPE assessment (e.g., a score). Each training pair may also include BPE segmented ground truth images corresponding to the input images. The configuration of the training pairs may vary across different embodiments. In some embodiments, the training pairs may include a single input image, a single ground truth BPE segmented image and/or a single BPE assessment. In other embodiments, the training pairs may include both of a morphological breast image and a contrast uptake image of the same breast, BPE segmented ground truth versions of the morphological breast image and the contrast enhanced image, and a single ground truth BPE assessment for both of the morphological breast image and the CEM image. In other embodiments, a greater number of images may be used as input images within a single training pair. However, each training pair may include a single ground truth BPE assessment.

In still other embodiments, a training pair may include non-image inputs into the BPE assessment model, such as clinical information of a patient of the breast. The clinical information may increase an accuracy and/or performance of the BPE assessment model during training. For example, the clinical information may include metadata and/or timing data of images (e.g., injection timing, time of acquisition), menstrual cycle information of the patient, an age of the patient, demographic data of the patient, a presence or absence of one or more conditions of the patient, or different clinical information. In some embodiments, an additional input into the BPE assessment model may be a definition of a specified portion of one or more input images that are to be excluded from the BPE assessment. For example, a suspicious ROI may have been previously detected or identified in the one or more input images. The suspicious ROI may include lesions or artifacts showing contrast uptake where BPE is not present, which may bias the BPE assessment. To ensure that the suspicious ROI does not bias the BPE assessment, the specified portion of the one or more input images including the suspicious ROI may be included in the training pair, and the specified portion may not be included in the adjustment of network parameters during training. For example, the area of the suspicious ROI may be identified with a CAD (Computer Aided Diagnosis) tool, which may be able to detect and highlight areas or ROIs in an image volume. In one embodiment, the CAD tool is a DL model trained to recognize cancerous tissues. The CAD may define a set of pixels/voxels including the suspicious ROI. Based on the CAD, the defined set of pixels/voxels may not be included as inputs into an input layer of the BPE assessment model. In this way, the BPE assessment model may generate BPE assessments during training based on portions of the image not including the suspicious ROI. To ensure that the model is trained to accept the CAD during a later inference stage, various training pairs of the training data may include such additional CAD inputs.

At 508, method 500 includes training the BPE assessment model to predict a BPE label or score and/or BPE segmentation for one or more breast images included in a training pair, using the training dataset generated at 506. In various embodiments, the BPE assessment model may be a deep learning (DL) neural network. In one embodiment, the BPE assessment model is a deep convolutional neural network (CNN). The CNN may include one or more convolutional layers, which in turn comprise one or more convolutional filters. The convolutional filters may comprise a plurality of weights, wherein the values of the weights are learned during a training procedure. The convolutional filters may correspond to one or more visual features/patterns, thereby enabling the BPE assessment model to identify and extract features from the images.

Training the BPE assessment model may include iteratively inputting one or more input images (and in some embodiments, associated clinical data) of training pairs into an input layer of the BPE assessment model. The BPE assessment model propagates the input images from the input layer, through one or more hidden layers, until reaching an output layer of the BPE assessment model, to generate an output, where the output is one or more of a BPE label, a BPE score, and/or one or more BPE segmented images corresponding to the one or more breast images. The BPE label may indicate a BIRADS BPE level: minimal/ mild/moderate/marked. The BPE score may indicate a percentage of breast tissues of the breast in the breast image(s) in which BPE is detected, with respect to a total surface area or volume of the breast. The BPE segmented images may indicate the areas of the breast or breast image identified as BPE.

The BPE assessment model may be configured to iteratively adjust one or more of the plurality of weights of the BPE assessment model in order to minimize, for each training pair, a difference between the output of the BPE assessment model and the ground truth BPE assessment included in the training pair. The difference (or loss) may be back-propagated through the BPE assessment model to update the weights (and biases) of the hidden (convolutional) layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the BPE assessment model is then updated by adding the negative of the product of the gradient determined (or approximated) for the weight (or bias) with a predetermined step size. Updating of the weights and biases may be repeated until the weights and biases of the BPE assessment model converge, or the rate of change of the weights and/or biases of the deep neural network for each iteration of weight adjustment are under a threshold. It should also be noted that back-propagation is used as an example, and that other optimization schemes are valid for fitting the BPE assessment model's parameters.

In order to avoid overfitting, training of the BPE assessment model may be periodically interrupted to validate a performance of the BPE assessment model on the validation image pairs, as described above in reference to FIG. 3. Training of the BPE assessment model may end when a performance of the BPE assessment model on the validation set converges (e.g., when an error rate on the validation set converges on or to within a threshold of a minimum value). In this way, the BPE assessment model may be trained to predict a BPE score of a new breast image during a subsequent inference stage.

After the BPE assessment model has been trained and validated, the trained BPE assessment model may be stored in a memory of the image processing system for use in breast examinations performed using the imaging system during the subsequent inference stage. For example, the trained BPE assessment model may be stored in an inference module of the image processing system (e.g., inference module 212).

Figure 6:
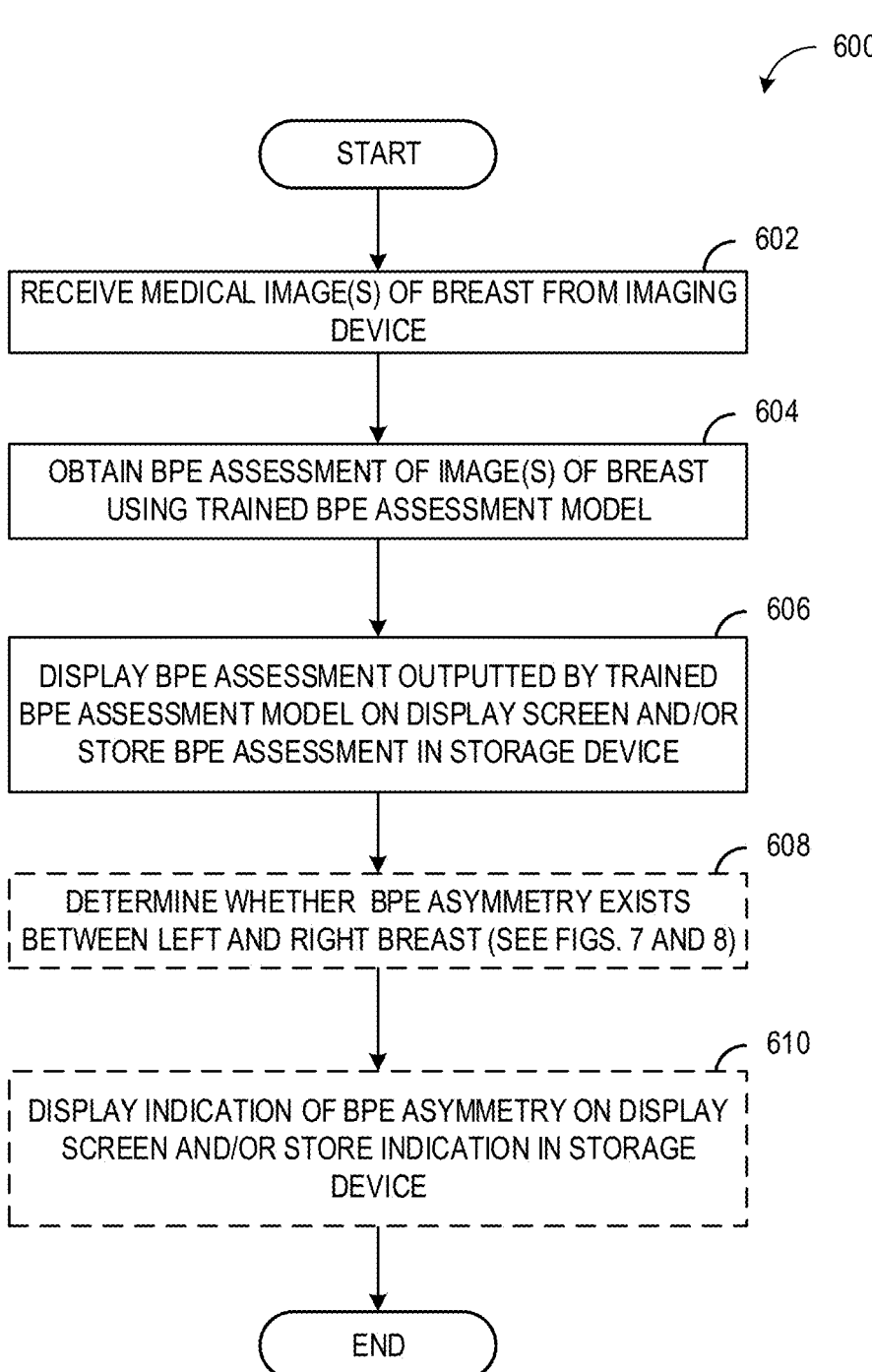
FIG. 6 is a flowchart illustrating a method for performing a BPE assessment of an image using the trained DL model, in accordance with one or more embodiments of the present disclosure.

Referring now to FIG. 6, an exemplary method 600 is shown for generating a BPE assessment of a breast of a patient of an imaging system, such as the imaging system 100 of FIG. 1, using a trained BPE assessment model, such as the BPE assessment model described above in reference to FIG. 5 (e.g., BPE assessment model 302 of FIG. 3). Generating the BPE assessment may include computing a BPE level of the breast as a score, where the score reflects a percentage of breast tissues of a surface area of a 2D image of the breast in which BPE is detected, or a percentage of breast tissues of a 3D image volume of the breast in which BPE is detected. The trained BPE assessment model may also output an image of the breast with BPE segmentation.

The BPE assessment may be performed in an automated manner, meaning, based on one or more images of the breast and without intervention by a human. Method 600 may be executed using computer readable instructions stored in the non-transitory memory of a computing device of an image processing system (e.g., imaging processing system 202 of FIG. 2) coupled to a controller of the imaging system (e.g., controller 44). In some embodiments, method 600 may be executed by another computing device without departing from the scope of this disclosure (e.g., an edge device, a picture archiving and communication system (PACS)).

Method 600 begins at 602, where method 600 includes receiving one or more medical images of a breast from the imaging system. In some examples, the one or more medical images may be stored in a memory of the imaging system or the image processing system (e.g., non-transitory memory 206 of FIG. 2). In other examples, the one or more medical images may be received from an imaging device of the imaging system during a breast exam (e.g., method 600 may be performed in real time during the breast exam). In some embodiments, the one or more medical images may include a first, contrast uptake image such as a recombined CEM image or CE-DBT image volume, and a second, low energy image such as a morphological image.

In some embodiments, the received one or more medical images of a breast may include a suspicious ROI that was previously detected or identified. The suspicious ROI may include lesions or artifacts showing contrast uptake where BPE is not present. As such, the suspicious ROI can bias the BPE assessment. When the suspicious ROI is present in the one or more medical images of a breast, an area of the suspicious ROI may be excluded from the BPE assessment. For example, the area of the suspicious ROI may be identified using a CAD tool. For example, the CAD may define a set of pixels/voxels of the received one or more medical images including the suspicious ROI. Based on the CAD, the defined set of pixels/voxels may not be included as inputs into the BPE assessment model. In this way, the BPE assessment model may output the BPE assessment based on the non-excluded pixels/voxels of the received one or more medical images, and not considering the defined set of pixels/voxels including the suspicious ROI.

At 604, method 600 includes obtaining a predicted BPE assessment of the medical image(s) using the trained BPE assessment model. Obtaining the predicted BPE assessment of the medical image(s) using the trained BPE assessment model may include inputting the medical image(s) into the trained BPE assessment model in a manner similar to that described above in reference to method 500, and receiving the predicted BPE assessment as an output of the trained BPE assessment model.

At 606, method 600 includes displaying the predicted BPE assessment (e.g., a BPE score or level) outputted by the BPE assessment model on a display device of the image processing system (e.g., display device 234). In preferred embodiments, the predicted BPE assessment may be displayed on the display device in real time, meaning as an examiner is performing the examination. In some embodiments, the predicted BPE assessment may be displayed along with (e.g., alongside) the image(s) of the breast inputted into the BPE assessment model. For example, the predicted BPE assessment may be displayed in a label superimposed on the image(s) of the breast. Additionally or alternatively, the predicted BPE assessment may be stored in a storage device of the imaging system or a different storage device.

As an example of an output of the BPE assessment model, FIG. 9 shows a first exemplary CEM image 900 of a breast of a patient, where BPE can be seen as a lighter portion 902 of CEM image 900. A BPE assessment 904 of the breast outputted by the BPE assessment model is shown superimposed on CEM image 900. In the embodiment depicted in FIG. 9, the BPE assessment 904 is a classification of the BPE as "moderate", based on an extent of the BPE indicated by lighter portion 902. Specifically, the BPE assessment model may be trained to output an encoding indicating a classification into categories such as "minimal", "mild", "moderate", or "marked", or a different set of categories, based on a ratio of lighter portion 902 with respect to a total surface area (or volume, for 3D image volumes) of the breast. For example, the BPE assessment model may be trained to output a binary string indicating a predicted category, such as 1000 for minimal, 0100 for mild, 0010 for moderate, or 0001 for marked, or a different type of encoding. Alternatively, the BPE assessment model may be trained to output a BPE score (e.g., the percentage), and the score may be converted into one or more classifications by applying a set of rules and/or thresholds to the score.

Additionally or alternatively, the score may be indicated on the image of the breast. For example, FIG. 10 shows a second exemplary CEM image 1000 of the breast of a patient, where CEM image 1000 may be a BPE segmented image outputted by the BPE assessment model. In FIG. 10, a BPE segmented portion 1002 of CEM image 1000 is shaded for clarity. A BPE assessment 1004 of the breast outputted by the BPE assessment model is shown superimposed on CEM image 1000, where BPE assessment 1004 is a BPE score indicating the percentage of lighter portion 902 with respect to the total surface area (or volume, for 3D image volumes) of the breast.

Returning to FIG. 6, at 608, method 600 optionally includes determining whether an asymmetry exists between a first BPE of a left breast of a patient, and a second BPE of a right breast of the patient. If the first BPE differs from the second BPE by more than a threshold difference, a user of the imaging system may be alerted. Because BPE asymmetry is linked to breast cancer development, detected asymmetries may be highlighted to the user, for example, in the form of a score or a warning, alongside the computed BPE levels. BPE asymmetry presence may impact a level of cancer suspicion and severity, ultimately impacting a patient care pathway. Determining whether the BPE asymmetry exists is described below in reference to FIGS. 7 and 8.

In some embodiments, method 600 may optionally include determining whether an asymmetry or inconsistency exists between different images or types of images of a same breast. For example, a first BPE score may be generated based on a first image of a breast using the BPE assessment model, and a second BPE score may be generated based on a second image of the same breast using the BPE assessment model. If a difference between the first BPE score and the second BPE score exceeds a threshold difference, a BPE score inconsistency may be displayed on the display device to alert a user of the imaging system.

At 610, method 600 includes displaying an indication of the BPE asymmetry (e.g., whether BPE asymmetry exists or not) on the display device and/or storing the indication of the BPE asymmetry in the storage device, and method 600 ends. In various embodiments, the indication of the BPE asymmetry may be displayed next to or superimposed on both of a first image of the left breast and a second image of the right breast, such that the BPE in the first image and the second image may be compared by a user of the imaging system (e.g., a radiologist).

FIG. 11 shows an exemplary BPE asymmetry display 1100 that may be displayed on the display screen, where the BPE asymmetry was not detected. BPE asymmetry display 1100 includes a first medical image 1102 of a left breast of a patient of an imaging system, alongside a second medical image 1104 of a right breast of the patient. In FIG. 11, a first BPE 1106 of the left breast shown in the first medical image 1102 and a second BPE 1108 of the right breast shown in the second medical image 1104 are approximately equivalent, and a first BPE assessment 1110 of the left breast displayed on the first medical image 1102 (e.g., 65%) is equal to a second BPE assessment 1112 of the right breast displayed on the second medical image 1104 (e.g., 65%). As a result, an indication 1114 that the BPE asymmetry was not detected is displayed in exemplary BPE asymmetry display 1100. It should be appreciated that the configuration of visual components of exemplary BPE asymmetry display 1100 is for illustrative purposes, and in other embodiments, first medical image 1102, second medical image 1104, first BPE assessment 1110, second BPE assessment 1112, and indication 1114 may be included in different locations, sizes, etc. in exemplary BPE asymmetry display 1100.

Figure 7:
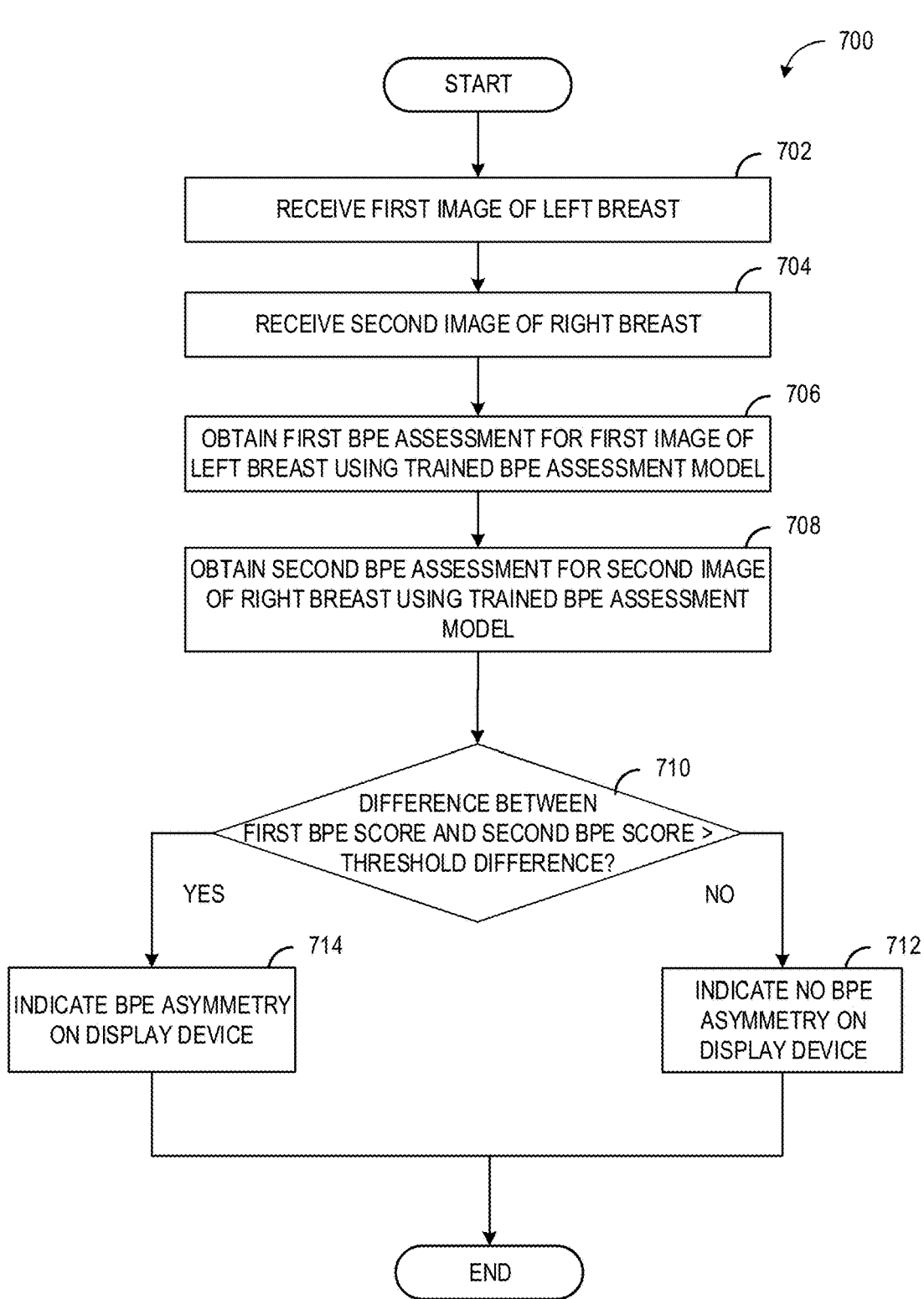
FIG. 7 is a first flowchart illustrating a first method for detecting an asymmetry between a BPE level of a first breast of a patient and a BPE level of a second breast of the patient, in accordance with one or more embodiments of the present disclosure.

Referring now to FIG. 7, a method 700 is shown for determining whether a BPE asymmetry exists between a first breast of a patient of an imaging system (e.g., left breast), and a second breast of the patient (e.g., right breast), using a trained BPE assessment model, such as the BPE assessment model described above in reference to FIG. 5. The imaging system may be a non-limiting example of the imaging system 100 of FIG. 1. The BPE asymmetry determination may be performed in an automated manner, meaning, based on images of the first breast and the second breast without intervention by a human. Method 700 may be executed using computer readable instructions stored in the non-transitory memory of a computing device of an image processing system (e.g., imaging processing system 202 of FIG. 2) coupled to a controller of the imaging system (e.g., controller 44). In various embodiments, method 700 may be performed as part of method 600 described above in reference to FIG. 6.

Method 700 begins at 702, where method 700 includes receiving a first image of the left breast of the patient, and at 704, method 700 includes receiving a second image of the right breast of the patient. The first image and the second image may be received from an imaging device of the imaging system, for example, during a breast examination of the patient, or the first image and the second image may be received from a storage device of the imaging system or image processing system. For example, the breast examination may be performed on the patient at a first time, and the breast BPE asymmetry may be determined in accordance with method 700 at a later time. During the breast examination, the first breast may be imaged, and the second breast may be subsequently imaged as part of the same examination.

At 706, method 700 includes obtaining a first BPE assessment (e.g., score) for the first image of the left breast using a trained BPE assessment model, such as trained BPE assessment model 322 of FIG. 3. The first BPE assessment may be obtained by following one or more steps of method 600 of FIG. 6 described above. Similarly, at 708, method 700 includes obtaining a second BPE assessment (e.g., score) for the second image of the right breast using the trained BPE assessment model, also in accordance with method 600.

At 710, method 700 includes determining whether a difference between the first BPE score and the second BPE score is greater than a threshold difference. For example, if the first BPE score is 65%, and the second BPE score is 55%, then the difference would be 10%. The threshold difference may be, for example, 5%, where the difference (10%) is greater than the threshold difference (5%), and the answer is YES. Alternatively, if the first BPE score is 65%, and the second BPE score is 62%, then the difference would be 3% (e.g., below 5%), where the answer is NO.

In some embodiments, the threshold difference may be variable. In one embodiment, the threshold difference may be a function of an injection time and/or acquisition time. For example, if the acquisition time between the first breast and the second breast is two minutes, the threshold could be set to 5%. If the acquisition time between the first breast and the second breast is 15 minutes, the threshold could be set to 25%. Because BPE evolves over time and a BPE assessment may depend on an amount of contrast uptake at a time that the BPE assessment is performed, the difference between the first BPE assessment and the second BPE assessment may be accounted for by a relative difference in contrast uptake, rather than BPE asymmetry. For this reason, the asymmetry threshold can vary depending on different injection/acquisition timing.

If at 710 it is determined that the difference between the first BPE score and the second BPE score is not greater than the threshold difference (e.g., NO), method 700 proceeds to 712. At 712, method 700 may include indicating that BPE asymmetry was not detected on the display device, and method 700 ends. In some embodiments, if the BPE asymmetry is not detected, no indication may be displayed on the display device. Alternatively, if at 710 it is determined that the difference between the first BPE score and the second BPE score is greater than the threshold difference (e.g., YES), method 700 proceeds to 714. At 714, method 700 includes indicating the BPE asymmetry on a display device of the imaging system, and method 700 ends.

Figure 8:
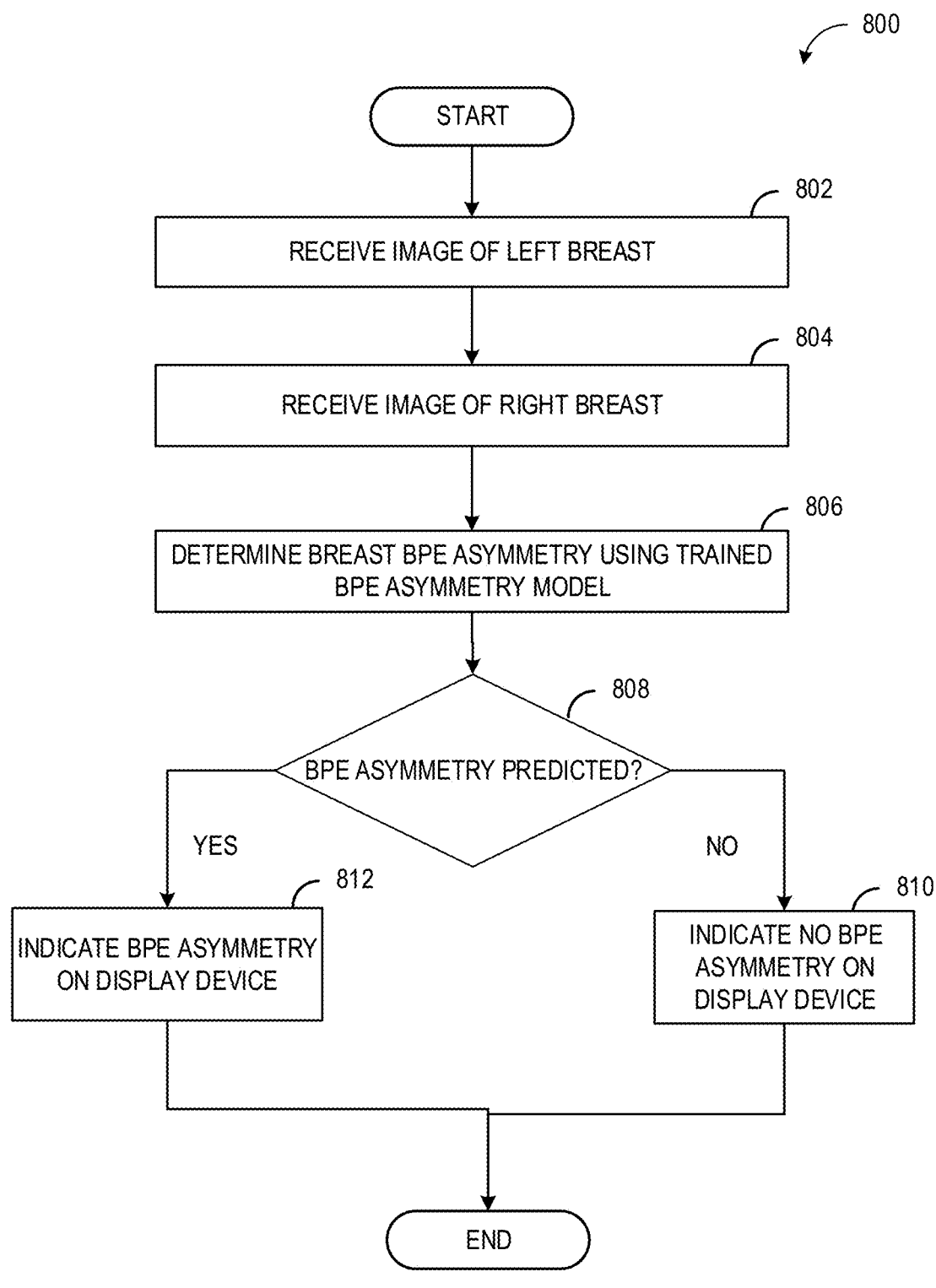
FIG. 8 is a second flowchart illustrating a second method for detecting an asymmetry between a BPE level of a first breast of a patient and a BPE level of a second breast of the patient, in accordance with one or more embodiments of the present disclosure.

FIG. 8 shows an alternative method 800 for determining whether the BPE asymmetry exists between the first breast of the patient (e.g., left breast), and the second breast of the patient (e.g., right breast), also using the trained BPE assessment model (of the image processing system of FIG. 2) described above in reference to FIG. 5 (e.g., BPE assessment model 322) and based on images generated by an imaging system such as the imaging system 100 of FIG. 1. However, for the purposes of method 800, the trained BPE assessment model may be trained to concurrently receive a first image of the first breast and a second image of the second breast as inputs, and output a prediction whether a first BPE assessment of the first breast is within a threshold difference of a second BPE assessment of the second breast. For example, the image processing system may include a trained BPE assessment model trained to predict a BPE score of a breast in an input image, and a trained BPE asymmetry model trained to predict a degree of asymmetry between two breasts of a same patient, in two different input images. The trained BPE assessment model may be used to generate individual BPE scores or classifications of breast images, and the trained BPE asymmetry model may be used to determine breast asymmetry as a separate task. Outputs of the trained BPE assessment model and the BPE asymmetry model may be combined and/or displayed together in a shared display, as in FIG. 11.

Alternative method 800 may also be performed in an automated manner, meaning, based on images of the first breast and the second breast without intervention by a human. Method 800 may be executed using computer readable instructions stored in the non-transitory memory of a computing device of an image processing system (e.g., imaging processing system 202 of FIG. 2) coupled to a controller of the imaging system (e.g., controller 44). In various embodiments, method 800 may be performed as part of method 600 described above in reference to FIG. 6, as an alternative to method 700.

Method 800 begins at 802, where method 800 includes receiving a first image of the left breast of the patient, and at 804, method 800 includes receiving a second image of the right breast of the patient. The first image and the second image may be received from an imaging device of the imaging system, for example, during a breast examination of the patient, or the first image and the second image may be received from a storage device of the imaging system or image processing system. For example, the breast examination may be performed on the patient at a first time, and the breast BPE asymmetry may be determined in accordance with method 800 at a later time. During the breast examination, the first breast may be imaged, and the second breast may be subsequently imaged as part of the same examination.

At 806, method 800 includes inputting the first image and the second image into the trained BPE asymmetry model, and receiving as an output, a prediction of whether breast BPE asymmetry exists. In various embodiments, the BPE asymmetry model may include as input either or both of an injection timing and an acquisition timing. The BPE asymmetry model may be trained on training pairs including injection and/or acquisition timings of images of left and right breasts, and the BPE asymmetry model may predict the BPE asymmetry based on a first acquisition and/or injection timing of the image of the left breast, and a second acquisition and/or injection timing of the image of the right breast. By using the acquisition and injection timing information, an accuracy of the BPE asymmetry model at predicting the BPE asymmetry may be increased.

At 808, if the breast BPE asymmetry is not predicted, method 800 proceeds to 810. At 810, method 800 includes indicating that BPE asymmetry was not detected on the display device, and method 800 ends. Alternatively, if at 808 the breast BPE asymmetry is predicted, method 800 proceeds to 812. At 812, method 800 includes indicating the BPE asymmetry on a display device of the imaging system, and method 800 ends.

Thus, a DL model-based approach to assessing breast BPE is proposed, where the DL model is trained to predict a level of BPE of one or both breasts of a patient of an imaging system, such as a digital mammography system or a DBT system, from one or more images acquired via the imaging system. The level of BPE may be assessed by inputting the one or more images into the DL model, and receiving a BPE assessment as output of the model. The one or more images may include one or more images of a same breast, where the BPE assessment outputted by the model may be a score, such as a percentage of BPE detected in either the images or portions of the images including the breast. The model may also be trained to output BPE segmented images of the one or both breasts. By performing the breast BPE assessment using the DL model rather than relying on a manual BPE assessment performed by a radiologist, the BPE assessment may be more accurate and/or more consistent across radiologists and/or across patients.

The more accurate BPE assessment may aid the radiologist in detecting lesions and/or differentiating lesions from normal breast tissues. By using a DL model to automatically perform breast BPE assessments, a workflow of the radiologist may be reduced or made more efficient, resulting in a decreased use of imaging system resources and an increase in available time of the radiologist to attend to other patients. In this way, an efficiency of an overall process of reading mammograms may be increased, leading to faster results for patients and more consistent, accurate diagnoses of cancer risk. As a result, patient outcomes may be improved.

Alternatively, the one or more images may include both an image of a left breast of the patient and a right breast of the patient, and the BPE assessment outputted by the model may be a prediction of whether BPE levels of both breasts are asymmetric (e.g., greater than a threshold difference). The model may be trained on pairs of images of both breasts. An accuracy of the DL model in detecting the asymmetry may be greater than an accuracy of a manual determination performed by a radiologist. Accurately detecting an asymmetry in the BPE levels of both breasts may increase an accuracy of a diagnosis of the patient, while reducing a time spent by the radiologist comparing images of both breasts.

The technical effect of using a DL model to automatically perform breast BPE assessments is that a the automatically performed BPE assessments may make it easier for a radiologist to detect lesions in a breast, and a workflow of the radiologist may be reduced or made more efficient, resulting in a decreased use of imaging system resources and an increase in available time of the radiologist to attend to other patients.

The disclosure also provides support for a method, comprising: performing an assessment of background parenchymal enhancement (BPE) of a breast of a patient based on one or more images of the breast acquired via an imaging system, using a deep learning (DL) model trained on different types of medical images of breasts, and displaying the one or more images and the BPE assessment at a display device, wherein the one or more images include at least one of: a contrast enhanced mammography (CEM) image, a contrast enhanced digital breast tomosynthesis (CE-DBT) image volume, a CEM biopsy image, and a synthetic two-dimensional (2D) image. In a first example of the method, an output of the DL model includes one or more images showing a segmentation of BPE within the breast, and the one or more images showing the segmentation of the BPE and the BPE assessment are displayed on the display device. In a second example of the method, optionally including the first example, performing the BPE assessment of the breast based on the one or more images of the breast using the DL model further comprises inputting at least two different types of images of the breast into the DL model, and receiving the BPE assessment as an output of the DL model. In a third example of the method, optionally including one or both of the first and second examples, the at least two different types of images include a recombined (REC) image generated from a low energy (LE) image and a high energy (HE) image. In a fourth example of the method, optionally including one or more or each of the first through third examples, the at least two different types of images of the breast include both of a LE image and a REC image. In a fifth example of the method, optionally including one or more or each of the first through fourth examples, performing the BPE assessment of the breast based on the one or more images of the breast using the DL model further comprises inputting additional clinical information into the DL model, and receiving the BPE assessment as an output of the DL model, the additional clinical information including at least one of: metadata of the one or more images, a timing of an injection of contrast into the patient, acquisition times of the one or more images, menstrual cycle information of the patient, an age of the patient, demographic data of the patient, a presence or absence of one or more conditions of the patient, and a definition of a specified portion of the one or more images, the specified portion to be excluded from the BPE assessment. In a sixth example of the method, optionally including one or more or each of the first through fifth examples: the one or more images include one of a 2D CEM image, where the BPE assessment is a score indicating a percentage of tissues of the breast showing BPE with respect to a surface area of the breast, and a three-dimensional (3D) CE-DBT image volume, where the BPE assessment is a score indicating a percentage of tissues of the breast showing BPE, with respect to a total volume of the breast. In a seventh example of the method, optionally including one or more or each of the first through sixth examples, the BPE assessment is a classification of the breast into one of a plurality of categories. In a eighth example of the method, optionally including one or more or each of the first through seventh examples, performing the BPE assessment of the breast based on the one or more images of the breast using the DL model further comprises determining whether an asymmetry is detected between a first BPE level of a first image of a first breast of the patient and a second BPE level of a second image of a second breast of the patient. In a ninth example of the method, optionally including one or more or each of the first through eighth examples, determining whether the asymmetry is detected between the first BPE level and the second BPE level further comprises: inputting the first image of the first breast into the DL model, and receiving a first BPE assessment of the first breast as a first output of the DL model, inputting the second image of the second breast into the DL model, and receiving a second BPE assessment of the second breast as a second output of the DL model, and in response to a difference between the first BPE assessment and the second BPE assessment being greater than a threshold difference, displaying an indication that the asymmetry was detected on the display device. In a tenth example of the method, optionally including one or more or each of the first through ninth examples, the DL model is trained to predict the asymmetry between the first BPE level and the second BPE level, and determining whether the asymmetry exists between the first BPE level and the second BPE level further comprises: inputting the first image of the first breast and the second image of the second breast into the DL model, and receiving a predicted BPE asymmetry between the first BPE level and the second BPE level as an output of the DL model, and displaying an indication of the predicted BPE asymmetry was detected on the display device. In a eleventh example of the method, optionally including one or more or each of the first through tenth examples, the method further comprises: determining whether the asymmetry exists between the first BPE level and the second BPE level based on a first time at which the first image was acquired and a second time at which the second image was acquired. In a twelfth example of the method, optionally including one or more or each of the first through eleventh examples, the method further comprises: acquiring a craniocaudal view (CC) and a mediolateral oblique (MLO) view of the breast during a CEM exam, and generating a BPE assessment of the breast using the DL model based on both of the CC and MLO views.

The disclosure also provides support for an image processing system, comprising: a display device, a processor and non-transitory memory storing instructions executable by the processor to: receive a first set of one or more medical images of a first breast of a patient acquired via an imaging system, input the first set of one or more medical images into a deep learning (DL) model, the DL model trained to perform an assessment of a first level of BPE of the first breast based on the first set of one or more medical images, receive a first BPE assessment of the first breast as an output of the DL model, the first BPE assessment including at least one of a score and a classification indicating a percentage of glandular tissues of the first breast showing BPE with respect to a surface or volume of the first breast, and display the first BPE assessment on the display device. In a first example of the system, further instructions are stored in the non-transitory memory that when executed, cause the processor to input additional information into the DL model along with the first set of one or more medical images, and generate the first BPE assessment of the first breast based on the first set of one or more medical images and the additional information, the additional information including at least one of: metadata of the one or more medical images, a timing of an injection of contrast into the patient, acquisition times of the one or more medical images, menstrual cycle information of the patient, an age of the patient, demographic data of the patient, a presence or absence of one or more conditions of the patient, and a definition of a specified portion of the one or more medical images, the specified portion to be excluded from the first BPE assessment. In a second example of the system, optionally including the first example, further instructions are stored in the non-transitory memory that when executed, cause the processor to: receive a second set of one or more medical images of a second breast of the patient, input the second set of one or more medical images into the DL model to obtain a second BPE assessment of a second level of BPE of the second breast based on the second set of one or more medical images, determine whether a BPE asymmetry exists between the first level of BPE of the first breast and the second level of BPE of the second breast, and in response to determining that the BPE asymmetry exists, display an indication that the BPE asymmetry was detected on the display device. In a third example of the system, optionally including one or both of the first and second examples, further instructions are stored in the non-transitory memory that when executed, cause the processor to determine whether the BPE asymmetry exists based on a first timing of a first acquisition of the first set of one or more medical images and a second timing of a second acquisition of the second set of one or more medical images. In a fourth example of the system, optionally including one or more or each of the first through third examples, on the one or more medical images include at least one of: a recombined contrast enhanced mammography (CEM) image, both of a low-energy morphological image and the recombined CEM image, a contrast enhanced digital breast tomosynthesis (CE-DBT) image volume, a CEM biopsy image, a synthetic two-dimensional (2D) image, and both of a craniocaudal (CC) view and a mediolateral oblique (MLO) view of the first breast acquired during a CEM exam. In a fifth example of the system, optionally including one or more or each of the first through fourth examples, the output of the DL model includes one or more images showing a segmentation of BPE within the first breast, and the one or more images showing the segmentation of the BPE and the BPE assessment are displayed on the display device.

The disclosure also provides support for a method for an imaging system, the method comprising: receiving a first set of one or more medical images of a first breast of a patient acquired via the imaging system at a first time, receiving a second set of one or more medical images of a second breast of the patient acquired via the imaging system at a second time, inputting at least the first set of one or more medical images, the second set of one or more medical images, the first time, and the second time into a deep learning (DL) model to obtain an assessment of a BPE asymmetry between the first breast and the second breast, displaying at least one image of the first set of medical images of the first breast on a display device of the imaging system, displaying at least one image of the second set of medical images of the second breast on the display device, and displaying an indication of the BPE asymmetry on the display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
training a deep learning (DL) model with a plurality of sets of training data from training subjects, each set of training data of the plurality of sets of training data including two input images of a breast of a respective one of the training subjects, ground truth versions of the two input images with background parenchymal enhancement (BPE) segmented, and a ground truth BPE score for both of the two input images, the DL model further trained with clinical information including contrast injection timing and acquisition timing for each set of training data, the two input images comprising a training low energy image and a training recombination image created from the training low energy image and a training high energy image;
obtaining a low energy image and a high energy image of a breast of a patient acquired with an x-ray imaging system configured to perform dual-energy imaging;
entering the low energy image and a recombination image generated from the low and high energy images of the breast of the patient acquired via the x-ray imaging system as input to the DL model;
receiving, as output from the DL model, a BPE assessment based on the low energy image and the recombination image of the breast of the patient; and
displaying the one or more images and the BPE assessment at a display device.

2. The method of claim 1, wherein an output of the DL model includes one or more images showing a segmentation of BPE within the breast, and the one or more images showing the segmentation of the BPE and the BPE assessment are displayed on the display device.

3. The method of claim 1, further comprising inputting additional clinical information into the DL model, and receiving the BPE assessment as an output of the DL model, the additional clinical information including at least one of:
metadata of the one or more images;
a timing of an injection of contrast into the patient;
acquisition times of the one or more images;
menstrual cycle information of the patient;
an age of the patient;
demographic data of the patient;
a presence or absence of one or more conditions of the patient; and
a definition of a specified portion of the one or more images, the specified portion to be excluded from the BPE assessment.

4. The method of claim 1, wherein:
the BPE assessment is a score indicating a percentage of tissues of the breast of the patient showing BPE with respect to a surface area of the breast; or wherein the BPE assessment is a score indicating a percentage of tissues of the breast of the patient showing BPE, with respect to a total volume of the breast.

5. The method of claim 1, wherein the BPE assessment is a classification of the breast of the patient into one of a plurality of categories.

6. The method of claim 1, wherein the breast is a first breast of the patient and the BPE assessment includes a first level of BPE of the first breast, and further comprising determining whether an asymmetry is detected between the first BPE level and a second BPE level of a second breast of the patient.

7. The method of claim 6, wherein determining whether the asymmetry is detected between the first BPE level and the second BPE level further comprises:
inputting a low energy image and a recombination image of the second breast into the DL model, and receiving a second BPE assessment of the second breast as a second output of the DL model, the second BPE assessment including the second BPE level; and
in response to a difference between the first BPE level and the second BPE level being greater than a threshold difference, displaying an indication that the asymmetry was detected on the display device.

8. The method of claim 6, wherein the DL model is trained to predict the asymmetry between the first BPE level and the second BPE level, and determining whether the asymmetry exists between the first BPE level and the second BPE level further comprises:
inputting the low energy image and the recombination image of the first breast and a low energy image and a recombination image of the second breast into the DL model, and receiving a predicted BPE asymmetry between the first BPE level and the second BPE level as an output of the DL model; and displaying an indication of the predicted BPE asymmetry was detected on the display device.

9. The method of claim 6, further comprising determining whether the asymmetry exists between the first BPE level and the second BPE level based on a first time at which the low energy image of the first breast was acquired and a second time at which the low energy image of the second breast was acquired.

10. The method of claim 1, further comprising acquiring a craniocaudal view (CC) and a mediolateral oblique (MLO) view of the breast of the patient during a CEM exam, and generating the BPE assessment of the breast of the patient using the DL model based on both of the CC and MLO views.

11. An image processing system, comprising:

a display device;

an x-ray imaging system configured to perform dual-energy imaging;

non-transitory memory storing instructions executable by one or more processors to:

train a deep learning (DL) model with a plurality of sets of training data from training subjects, each set of training data of the plurality of sets of training data including two input images of a breast of a respective one of the training subjects, ground truth versions of the two input images with background parenchymal enhancement (BPE) segmented, and a ground truth BPE score for both of the two input images, the two input images comprising a training low energy image and a training recombination image created from the low energy image and a training high energy image;

receive a first set of medical images of a first breast of a patient acquired via the x-ray imaging system, the first set of medical images of the first breast including a low energy image and a first high energy image;

input the the first low energy image and a first recombination image generated from the low energy image and the first high energy image into the DL model, the DL model trained to perform an assessment of a first level of BPE of the first breast based on the first low energy image and the first recombination image;

receive a first BPE assessment of the first breast as an output of the DL model, the first BPE assessment including at least one of a score and a classification indicating a percentage of glandular tissues of the first breast showing BPE with respect to a surface or volume of the first breast; and display the first BPE assessment on the display device.

12. The image processing system of claim 11, wherein further instructions are stored in the non-transitory memory that when executed, cause the processor to input additional information into the DL model, and generate the first BPE assessment of the first breast based on the first low energy image and the first recombination image and the additional information, the additional information including at least one of:

metadata of the one or more medical images;

a timing of an injection of contrast into the patient;

acquisition times of the one or more medical images;

menstrual cycle information of the patient;

an age of the patient;

demographic data of the patient;

a presence or absence of one or more conditions of the patient; and a definition of a specified portion of the one or more medical images, the specified portion to be excluded from the first BPE assessment.

13. The image processing system of claim 11, wherein further instructions are stored in the non-transitory memory that when executed, cause the processor to:

receive a second set of medical images of a second breast of the patient acquired with the x-ray imaging system, the second set including a second low energy image of the second breast and a second high energy image of the second breast;

input the second low energy image and a second recombination image generated from the second low energy image and the second high energy image into the DL model to obtain a second BPE assessment of a second level of BPE of the second breast based on the second low energy image and the second recombination image;

determine whether a BPE asymmetry exists between the first level of BPE of the first breast and the second level of BPE of the second breast; and in response to determining that the BPE asymmetry exists, display an indication that the BPE asymmetry was detected on the display device.

14. The image processing system of claim 13, wherein further instructions are stored in the non-transitory memory that when executed, cause the processor to determine whether the BPE asymmetry exists based on a first timing of a first acquisition of the first set of medical images and a second timing of a second acquisition of the second set of medical images.

15. The image processing system of claim 11, wherein the output of the DL model includes one or more images showing a segmentation of BPE within the first breast, and the one or more images showing the segmentation of the BPE and the BPE assessment are displayed on the display device.

16. A method for an x-ray imaging system configured to perform dual-energy imaging, the method comprising:

training a deep learning (DL) model with a plurality of sets of training data from training subjects, each set of training data of the plurality of sets of training data including two input images of a breast of a respective one of the training subjects, ground truth versions of the two input images with background parenchymal enhancement (BPE) segmented, and a ground truth BPE score for both of the two input images, the two input images comprising a training low energy image and a training recombination image created from the training low energy image and a training high energy image;

receiving a plurality of medical images of breasts of a patient acquired via the x-ray imaging system during a breast exam of the patient, the x-ray imaging system configured to obtain different views of the breasts at different times of the breast exam, the plurality of medical images including a first set of medical images of a first breast of the patient acquired via the imaging system at a first time of the breast exam and a second set of medical images of a second breast of the patient acquired via the imaging system at a second time of the breast exam, wherein the first set of medical images includes a first low energy image and a first high energy image, and wherein the second set of medical images includes a second low energy image and a second high energy image;

inputting the first low energy image, the second low energy image, a first recombination image generated from the first low energy image and the first high energy image, a second recombination image generated from the second low energy image and the second high energy image, the first time, and the second time into the DL model to obtain an assessment of a BPE asymmetry between the first breast and the second breast;

displaying at least one image of the first set of medical images of the first breast on a display device of the imaging system;

displaying at least one image of the second set of medical images of the second breast on the display device; and displaying an indication of the BPE asymmetry on the display device.

* * * * *